(12) United States Patent
Csavoy et al.

(10) Patent No.: US 8,467,852 B2
(45) Date of Patent: Jun. 18, 2013

(54) METHOD AND APPARATUS FOR PERFORMING A NAVIGATED PROCEDURE

(75) Inventors: Andrew N. Csavoy, Minneapolis, MN (US); Matthew S. Solar, Indialantic, FL (US); Jeffrey M. Waynik, Nederland, CO (US); Mark S. Freas, Palm Bay, FL (US); Thomas I. Miller, Palm Bay, FL (US); Keith Sootsman, Kalamazoo, MI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/286,734

(22) Filed: Nov. 1, 2011

(65) Prior Publication Data
US 2012/0046542 A1 Feb. 23, 2012

Related U.S. Application Data

(63) Continuation of application No. 12/110,666, filed on Apr. 28, 2008, which is a continuation-in-part of application No. 11/739,401, filed on Apr. 24, 2007.

(51) Int. Cl.
*A61B 5/05* (2006.01)

(52) U.S. Cl.
USPC .......................................... 600/424; 600/429

(58) Field of Classification Search
None
See application file for complete search history.

(56) References Cited

U.S. PATENT DOCUMENTS

| | | | |
|---|---|---|---|
| 5,370,118 A | 12/1994 | Vij et al. | |
| 5,570,182 A | 10/1996 | Nathel et al. | |
| 5,577,503 A | 11/1996 | Bonutti | |
| 5,592,939 A | 1/1997 | Martinelli | |
| 5,676,673 A | 10/1997 | Ferre et al. | |
| 5,682,890 A | 11/1997 | Kormos et al. | |
| 5,740,808 A | 4/1998 | Panescu et al. | |
| 5,762,064 A | 6/1998 | Polvani | |
| 5,772,594 A | 6/1998 | Barrick | |
| 5,868,675 A | 2/1999 | Henrion et al. | |
| 5,871,445 A | 2/1999 | Bucholz | |
| 5,913,820 A | 6/1999 | Bladen et al. | |
| 5,938,599 A | 8/1999 | Rasche et al. | |
| 5,983,126 A | 11/1999 | Wittkampf | |
| 6,006,126 A | 12/1999 | Cosman | |
| 6,011,996 A | 1/2000 | Gielen et al. | |

(Continued)

FOREIGN PATENT DOCUMENTS

| | | |
|---|---|---|
| EP | 1743591 A2 | 1/2007 |
| FR | 2798295 | 3/2001 |

(Continued)

OTHER PUBLICATIONS

"3M Surgical Drapes, Drape Selection Guide," brochure, 3M copyright 2002, 2003, 2005.

(Continued)

*Primary Examiner* — Long V. Le
*Assistant Examiner* — Bo J Peng
(74) *Attorney, Agent, or Firm* — Harness, Dickey & Pierce PLC

(57) ABSTRACT

A system can be used to navigate or guide an instrument or device into an anatomy of a patient. The navigation can occur with the use of image data acquired of the patient. The image data can be registered to the patient space for navigation. Also, one or more coils can be used for tracking or localization.

22 Claims, 8 Drawing Sheets

U.S. PATENT DOCUMENTS

| | | | |
|---|---|---|---|
| 6,015,406 | A | 1/2000 | Goble et al. |
| 6,033,415 | A | 3/2000 | Mittelstadt et al. |
| 6,078,841 | A | 6/2000 | Kuzma |
| 6,084,411 | A | 7/2000 | Giaquinto et al. |
| 6,106,464 | A | 8/2000 | Bass et al. |
| 6,117,143 | A | 9/2000 | Hynes et al. |
| 6,122,541 | A | 9/2000 | Cosman et al. |
| 6,195,580 | B1 | 2/2001 | Grable |
| 6,205,411 | B1 | 3/2001 | DiGioia, III et al. |
| 6,235,038 | B1 | 5/2001 | Hunter et al. |
| 6,246,900 | B1 | 6/2001 | Cosman et al. |
| 6,273,896 | B1 | 8/2001 | Franck et al. |
| 6,301,492 | B1 | 10/2001 | Zonenshayn |
| 6,311,082 | B1 | 10/2001 | Creighton, IV et al. |
| 6,351,662 | B1 | 2/2002 | Franck et al. |
| 6,368,329 | B1 | 4/2002 | Truwit |
| 6,381,485 | B1 | 4/2002 | Hunter et al. |
| 6,405,072 | B1 | 6/2002 | Cosman |
| 6,413,263 | B1 | 7/2002 | Lobdill et al. |
| 6,474,341 | B1 | 11/2002 | Hunter et al. |
| 6,477,400 | B1 | 11/2002 | Barrick |
| 6,482,182 | B1 | 11/2002 | Carroll et al. |
| 6,490,475 | B1 | 12/2002 | Seeley et al. |
| 6,491,699 | B1 | 12/2002 | Henderson et al. |
| 6,493,573 | B1 | 12/2002 | Martinelli et al. |
| 6,516,212 | B1 | 2/2003 | Bladen et al. |
| 6,529,765 | B1 | 3/2003 | Franck et al. |
| 6,546,277 | B1 | 4/2003 | Franck et al. |
| 6,606,521 | B2 | 8/2003 | Paspa et al. |
| 6,618,612 | B1 | 9/2003 | Acker et al. |
| 6,662,036 | B2 | 12/2003 | Cosman |
| 6,704,957 | B2 | 3/2004 | Rhodes |
| 6,752,812 | B1 | 6/2004 | Truwit |
| 6,826,423 | B1 | 11/2004 | Hardy et al. |
| 6,829,508 | B2 | 12/2004 | Schulman et al. |
| 6,847,849 | B2 | 1/2005 | Mamo et al. |
| 6,862,805 | B1 | 3/2005 | Kuzma et al. |
| 6,896,675 | B2 | 5/2005 | Leung et al. |
| 7,033,326 | B1 | 4/2006 | Pianca et al. |
| 7,130,676 | B2 | 10/2006 | Barrick |
| 7,177,701 | B1 | 2/2007 | Pianca |
| 7,206,627 | B2 | 4/2007 | Abovitz et al. |
| 7,217,276 | B2 | 5/2007 | Henderson et al. |
| 7,235,084 | B2 | 6/2007 | Skakoon et al. |
| 7,313,430 | B2 | 12/2007 | Urquhart et al. |
| 7,619,416 | B2 | 11/2009 | Nordmeyer-Massner et al. |
| 7,747,312 | B2 | 6/2010 | Barrick et al. |
| 7,751,865 | B2 | 7/2010 | Jascob et al. |
| 2001/0011175 | A1 | 8/2001 | Hunter et al. |
| 2001/0014820 | A1 | 8/2001 | Gielen et al. |
| 2001/0034530 | A1 | 10/2001 | Malackowski et al. |
| 2002/0042619 | A1 | 4/2002 | Dominguez et al. |
| 2002/0072737 | A1 | 6/2002 | Belden et al. |
| 2002/0087101 | A1 | 7/2002 | Barrick et al. |
| 2002/0111634 | A1 | 8/2002 | Stoianovici et al. |
| 2002/0183608 | A1 | 12/2002 | Marmulla et al. |
| 2003/0009207 | A1 | 1/2003 | Paspa et al. |
| 2003/0078569 | A1 | 4/2003 | Caldera et al. |
| 2003/0097061 | A1 | 5/2003 | Ferre et al. |
| 2003/0114752 | A1 | 6/2003 | Henderson et al. |
| 2003/0163040 | A1 | 8/2003 | Gildenberg |
| 2003/0187351 | A1 | 10/2003 | Franck et al. |
| 2004/0092815 | A1 | 5/2004 | Schweikard et al. |
| 2004/0147839 | A1 | 7/2004 | Moctezuma de la Barrera et al. |
| 2004/0147851 | A1 | 7/2004 | Bignall |
| 2004/0152972 | A1* | 8/2004 | Hunter ............... 600/424 |
| 2004/0199072 | A1* | 10/2004 | Sprouse et al. ........... 600/424 |
| 2004/0215071 | A1 | 10/2004 | Frank et al. |
| 2005/0049486 | A1* | 3/2005 | Urquhart et al. .......... 600/429 |
| 2005/0075649 | A1 | 4/2005 | Bova et al. |
| 2005/0085714 | A1 | 4/2005 | Foley et al. |
| 2005/0085715 | A1 | 4/2005 | Dukesherer et al. |
| 2005/0085720 | A1 | 4/2005 | Jascob et al. |
| 2005/0119587 | A1 | 6/2005 | Roessler et al. |
| 2005/0198849 | A1 | 9/2005 | Goeggelmann et al. |
| 2005/0226377 | A1 | 10/2005 | Wong et al. |
| 2006/0058683 | A1 | 3/2006 | Chance |
| 2006/0190054 | A1 | 8/2006 | Malinowski et al. |
| 2006/0212044 | A1 | 9/2006 | Bova et al. |
| 2006/0241406 | A1 | 10/2006 | Noujeim |
| 2006/0253181 | A1 | 11/2006 | Schulman et al. |
| 2007/0015991 | A1 | 1/2007 | Fu et al. |
| 2007/0027385 | A1 | 2/2007 | Brister et al. |
| 2007/0167722 | A1 | 7/2007 | Bladen et al. |
| 2008/0204021 | A1 | 8/2008 | Leussler et al. |
| 2008/0269599 | A1 | 10/2008 | Csavoy et al. |
| 2008/0269600 | A1 | 10/2008 | Csavoy et al. |
| 2008/0269602 | A1* | 10/2008 | Csavoy et al. ................ 600/426 |
| 2008/0269777 | A1 | 10/2008 | Appenrodt et al. |
| 2009/0012509 | A1 | 1/2009 | Csavoy et al. |
| 2009/0261828 | A1 | 10/2009 | Nordmeyer-Massner et al. |
| 2010/0160771 | A1 | 6/2010 | Gielen et al. |

FOREIGN PATENT DOCUMENTS

| | | |
|---|---|---|
| GB | 2352512 | 1/2001 |
| WO | WO-9608209 | 3/1996 |
| WO | WO-9611624 A2 | 4/1996 |
| WO | WO-9833451 | 8/1998 |
| WO | WO-0050859 | 8/2000 |
| WO | WO-0224094 | 3/2002 |
| WO | WO-2004044612 | 5/2004 |
| WO | WO-2004100767 | 11/2004 |
| WO | WO-2005039386 | 5/2005 |
| WO | WO-2007002926 | 1/2007 |
| WO | WO-2008036050 | 3/2008 |

OTHER PUBLICATIONS

"Fazer® Contour Laser," 9730732, rev. 3 Aug. 2006. 9 Sheets.

"GE-OEC 9600 Digital Mobile C-Arm", Product-Support info from http/www.orsupport.com/products. (2006).

"Medtronic O-Arm Multi-Dimensional Surgical Imaging System"; Brochure, 24pp, 2009.

"Medtronic, LandmarX®, ENT Image Guidance System, FESS Frame", Instructions for Use (Jan. 2006), from website: http://www.medtronicent-techcomms.com/inserts-web/68E3580_D.pdf, accessed Mar. 29, 2012.

"microTargeting Drive System for Stereotactice Positioning" FHC, Inc., Mar. 2006.

"microTargeting® Drive System for Stereotactic Positioning," User Manual L011-1006B, Mar. 2006.

"Navigus, NexFrame, StimLoc", IGN—Image Guided Neurologics, copyright 2004, printed from www.igneurologics.com on Jul. 9, 2007, (2 sheets).

"NeuroNav™," *Alpha Omega Defining Neuroscience Technology*, http://www.alphaomega-eng.com/pr_site/neuronav/index.htm, Web. accessed Apr. 1, 2010.

"NexDrive™ Micro-Positioner, Microelectrode Recording & DBS™ Electrode Implantation," Medtronic, Inc. copyright 2006. (2 sheets).

"Nexframe Reticle System, Trajectory Orientation," Medtronic, Inc. copyright 2006. (2 sheets).

"NexFrame System—Case: Bilateral Activa Lead Delivery to STN Using Nexframe," IGN Image Guided Neurologics, Inc. copyright 2004. Printed from www.igneurologics.com on Jul. 9, 2007. (2 sheets).

"Nexframe," 2 sheets printed from www.igneurologics.com on Jul. 9, 2007.

"Passive Headrest, Full Head and Neck Support," Medtronic, Inc. copyright 2006, (2 sheets).

"PoleStar N20 iMRI Navigation Suite", Medtronic Navigation brochure, (2006), 2pp.

"StealthStation® TRIA™ plus Treatment Guidance System," brochure, Medtronic Surgical Navigation Technologies (2004) 2 pages.

"Stimloc™ Lead Securement Device," Medtronic, Inc. 2006. (2 sheets).

"The DBS Solution, Enabling Technologies, Case Studies," Medtronic, Inc. copyright 2006.

"The NexFrame System, Stereotactic Technology," Medtronic, Inc. copyright 2006. (3 sheets).

"Tracer™ Registration Feature", 9731369, rev. 2 Sep. 2004. 3 sheets.
"TREON, StealthStation," brochure, Medtronic Surgical Navigation Technologies (2001) 8 pages.
"Unibody™ Fiducials, Unibody Fiducial Marker," Medtronic, Inc. copyright 2006, (2 sheets).
Communication Relating to the Results of the Partial International Search for PCT/US2007/010164 included as part of Invitation to Pay Additional Fees mailed Feb. 21, 2008.
Final Office Action mailed Apr. 13, 2011 for U.S. Appl. No. 11/739,424.
Final Office Action mailed Dec. 3, 2010 for U.S. Appl. No. 11/739,401.
Final Office Action mailed Feb. 11, 2011 for U.S. Appl. No. 12/110,666.
Final Office Action mailed Oct. 14, 2011 for U.S. Appl. No. 12/062,605.
Foley, "The StealthStation: Three-Dimensional Image-Interactive Guidance for the Spine Surgeon," Spinal Frontiers, Apr. 1996, pp. 7-9.
International Preliminary Report on Patentability and Written Opinion for PCT/US2007/009928 mailed Nov. 5, 2009 claiming benefit of U.S. Appl. No. 11/739,401, filed Apr. 24, 2007.
International Preliminary Report on Patentability and Written Opinion for PCT/US2007/010121 issued Oct. 27, 2009 claiming benefit of U.S. Appl. No. 11/739,424, filed Apr. 24, 2007.
International Preliminary Report on Patentability and Written Opinion for PCT/US2007/010164 mailed Nov. 5, 2009 claiming benefit of U.S. Appl. No. 11/739,791, filed Apr. 25, 2007.
International Search Report and Written Opinion for case PCT/US2008/060316 mailed Jul. 11, 2008.
International Search Report and Written Opinion for PCT/US2007/009928 mailed on Mar. 26, 2008.
International Search Report and Written Opinion for PCT/US2007/010121 mailed Jan. 24, 2008.
International Search Report and Written Opinion for PCT/US2007/010164 mailed May 30, 2008 claiming benefit of U.S. Appl. No. 11/739,791, filed Apr. 25, 2007.
International Search Report and Written Opinion for PCT/US2007/010164 mailed May 30, 2008.
International Search Report and Written Opinion for PCT/US2008/082961 mailed Mar. 3, 2009 claiming benefit of U.S. Appl. No. 12/110,666, filed Apr. 28, 2008, which claims priority to U.S. Appl. No. 11/739,401, filed Apr. 24, 2007.
Interview Summary mailed Aug. 18, 2011 for U.S. Appl. No. 12/062,605.
Interview Summary mailed Feb. 2, 2011 for U.S. Appl. No. 11/739,424.
Johnson, Jennie et al., "Independently movable multielectrode array to record multiple fast-spiking neurons in the cerebral cortex during cognition" Methods, vol. 30, 2003, pp. 64-78, XP002465099 sections 2.2., 3.2; figures 1,2.
Leksell Stereotactic System® brochure, ELEKTA (undated) 6 pages.
Leksell Stereotactic System® http://www.elekta.com/healthcare__international_leksell_stereotactic_system.php (accessed May 20, 2009).
Notice of Allowance mailed Dec. 30, 2011 for U.S. Appl. No. 11/739,424.
Notice of Allowance mailed Jun. 9, 2011 for U.S. Appl. No. 11/739,401.
Notice of Allowance mailed May 12, 2011 for U.S. Appl. No. 12/110,666.
Notice of Allowance mailed Sep. 14, 2011 for U.S. Appl. No. 11/739,424.
Office Action mailed Aug. 19, 2010 for U.S. Appl. No. 11/739,401.
Office Action mailed May 11, 2011 for U.S. Appl. No. 12/062,605.
Office Action mailed Oct. 27, 2010 for U.S. Appl. No. 11/739,424.
Office Action mailed Sep. 15, 2010 for U.S. Appl. No. 12/110,666.
Office Communication and Issue Classification mailed Oct. 7, 2011 for U.S. Appl. No. 11/739,424.
Restriction Requirement mailed Feb. 1, 2012 for U.S. Appl. No. 12/626,223.
Restriction Requirement mailed Jul. 19, 2010 for U.S. Appl. No. 12/110,666.
Rosenow, Joshua, "Application Accuracy of an Electromagnetic Field-Based Image-Guided Navigation System," Stereotactic Fuct Neurosurg 2007; 85:75-81, Dec. 12, 2006.

* cited by examiner

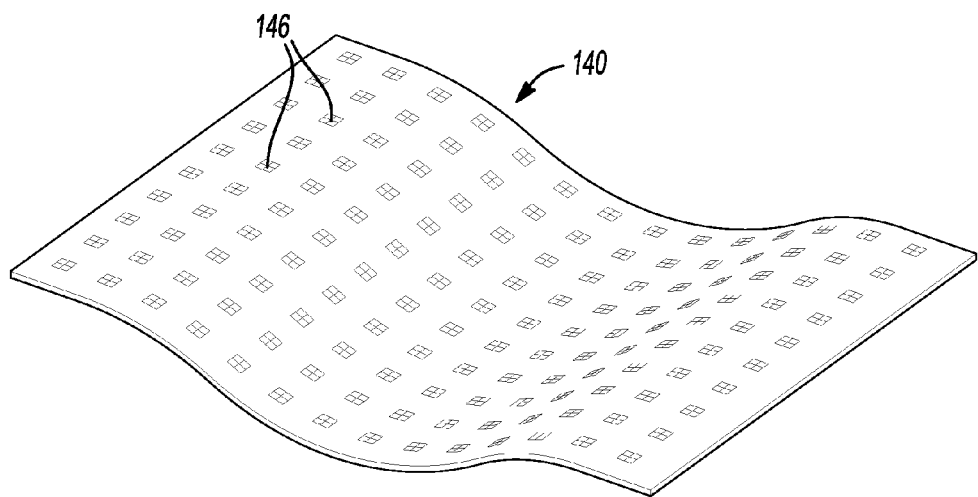
_Fig-4_
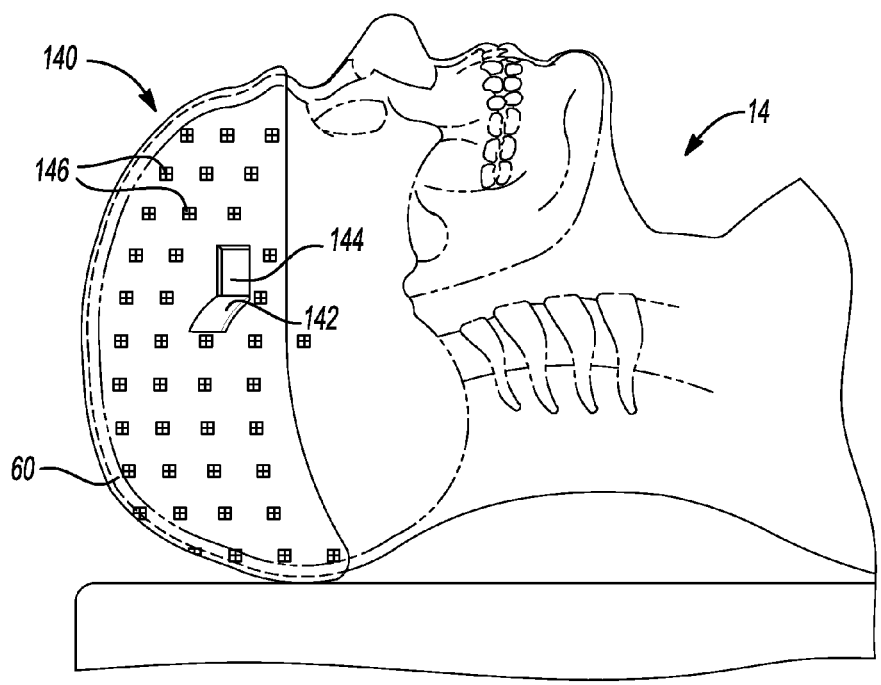
_Fig-5_

METHOD AND APPARATUS FOR PERFORMING A NAVIGATED PROCEDURE

CROSS-REFERENCE TO RELATED APPLICATIONS

This application is a continuation of U.S. patent application Ser. No. 12/110,666 filed on Apr. 28, 2008, which is a continuation-in-part of U.S. patent application Ser. No. 11/739,401 filed on Apr. 24, 2007. This application includes subject matter also disclosed in U.S. patent application Ser. No. 11/739,424, filed Apr. 24, 2007, entitled "FLEXIBLE ARRAY FOR USE IN NAVIGATED SURGERY and U.S. patent application Ser. No. 12/062,605, filed Apr. 4, 2008, entitled "NAVIGATED SOFT TISSUE PENETRATING LASER SYSTEM." The disclosures of the above applications are incorporated herein by reference.

FIELD

The present disclosure relates to a surgical navigation system, and particularly to a method and apparatus for navigating instruments.

BACKGROUND

The statements in this section merely provide background information related to the present disclosure and may not constitute prior art.

In an anatomy, such as a human anatomy, various anatomical portions and functions maybe damaged or require repair after a period of time. The anatomical portion or function maybe injured due to wear, aging, disease, or exterior trauma. To assist the patient, a procedure may be performed that may require access to an internal region of the patient through an incision. Due to exterior soft tissue, visualization of portions of the interior of the anatomy maybe difficult or require a large opening in the patient.

Image data maybe required of a patient to assist in planning, performing, and post operative analysis of a procedure. For example, magnetic resonance image data can be acquired of the patient to assist in diagnosing and planning a procedure. The image data acquired of the patient can also be used to assist in navigating various instruments relative to the patient while performing a procedure.

It is known to fixedly interconnect fiducial markers with a patient while imaging the patient and substantially using the fiducial markers that are imaged in the image data to correlate or register the image data to patient space. The fiducial markers, to ensure maximum reliability, however, are generally fixed directly to a bone of the patient. It is desirable, in various procedures, to substantially minimize or eliminate the invasiveness of inserting the fiducial markers into the bone through the skin of the patient. It is also desirable to provide an efficient mechanism to allow for registration of the image space to the physical space without requiring a separate procedure to implant one or more fiducial markers. It is also desirable to provide a system that allows for registration of the image space to the patient space without requiring a user to touch or contact one or more fiducial markers on a patient.

SUMMARY

During a surgical procedure on an anatomy, such as a human anatomy, instruments, implants, prosthesis, leads, electrodes and the like can be positioned in the anatomy. The various instruments or devices are generally positioned through incisions formed in soft tissue and/or hard tissue, such as the dermis and the cranium, of the anatomy. Therefore, anatomy of the patient can obscure or limit visualization of the devices in the anatomy during the procedure. It may be desirable, therefore, to provide a mechanism to determine a position of the devices within the anatomy.

According to various embodiments, a system to register image space to physical space of a patient for a surgical navigation procedure is disclosed. The system can include a first dynamic reference frame that can be attached relative to the patient in a first manner and a second dynamic reference frame that can be attached to the patient in a second manner. A tracked device can be used to determine a fiducial point on the patient. A processor can correlate the fiducial point on the patient to an image fiducial point in the image data. A tracking system can track at least one of the tracked devices, the first dynamic reference frame, the second dynamic reference frame, or combinations thereof. The processor can register the image space and physical space with the first dynamic reference frame with a first accuracy and can register the image space and physical space with the second dynamic reference frame with a second accuracy.

According to various embodiments, a method to register image space to physical space of a patient for a surgical navigation procedure is taught. The method can include acquiring image data of the patient defining the image space and including an image fiducial point and identifying the image fiducial point in the image data. A first dynamic reference frame can be attached to the patient in a first manner and a first registration of the image space to the physical space having a first accuracy can be performed with the attached first dynamic reference frame. A second dynamic reference frame can be attached to the patient in a second manner and a second registration of the image space to the physical space having a second accuracy can be performed with the attached second dynamic reference frame.

According to various embodiments, a method to register image space to physical space of a patient for a surgical navigation procedure is disclosed. The method can include attaching a fiducial marker with the patient and acquiring image data of the patient including an image fiducial point produced by the fiducial marker. The method can also include non-invasively attaching a first dynamic reference frame to the patient in a first manner, performing a first registration of the image data to the physical space having a first accuracy with the attached first dynamic reference frame, and navigating a first procedure with the performed first registration. The method can further include invasively attaching a second dynamic reference frame to the patient in a second manner, performing a second registration of the image data to the physical space having a second accuracy with the connected second dynamic reference frame, and navigating a second procedure with the performed second registration.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 4 is a detailed view of a flexible member including tracking devices, according to various embodiments;

FIG. 5 is a detailed environmental view of a flexible member including a plurality of tracking devices;

DETAILED DESCRIPTION

The following description is merely exemplary in nature and is not intended to limit the present disclosure, application, or uses. Although the following description illustrates and describes a procedure relative to a cranium of a patient, the current disclosure is not to be understood to be limited to such a procedure. For example, a procedure can also be performed relative to a spinal column, heart, vascular system, etc. Therefore, discussion herein relating to a specific region of the anatomy will be understood to be applicable to all regions of the anatomy, unless specifically described otherwise.

As discussed herein various systems and elements can be used to assist in a surgical procedure. For example, image data can be acquired of a patient to assist in illustrating the location of an instrument relative to a patient. Generally, image space can be registered to patient space to assist in this display and navigation. Fiducial markers can be affixed to the patient during imaging and registration or fiducial marker-less systems can be used. Fiducial marker-less systems can use other techniques, including surface or contour matching, as discussed herein. Various techniques can be used in fiducial marker-less systems, including, but not limited to, soft tissue penetrating laser systems, flexible members including tracking devices, etc. Also, procedures can include two registration procedures, including a course and a fine registration. The two registrations can allow for lessoning invasiveness of the procedure and increasing efficiency of the procedure.

Figure 1:
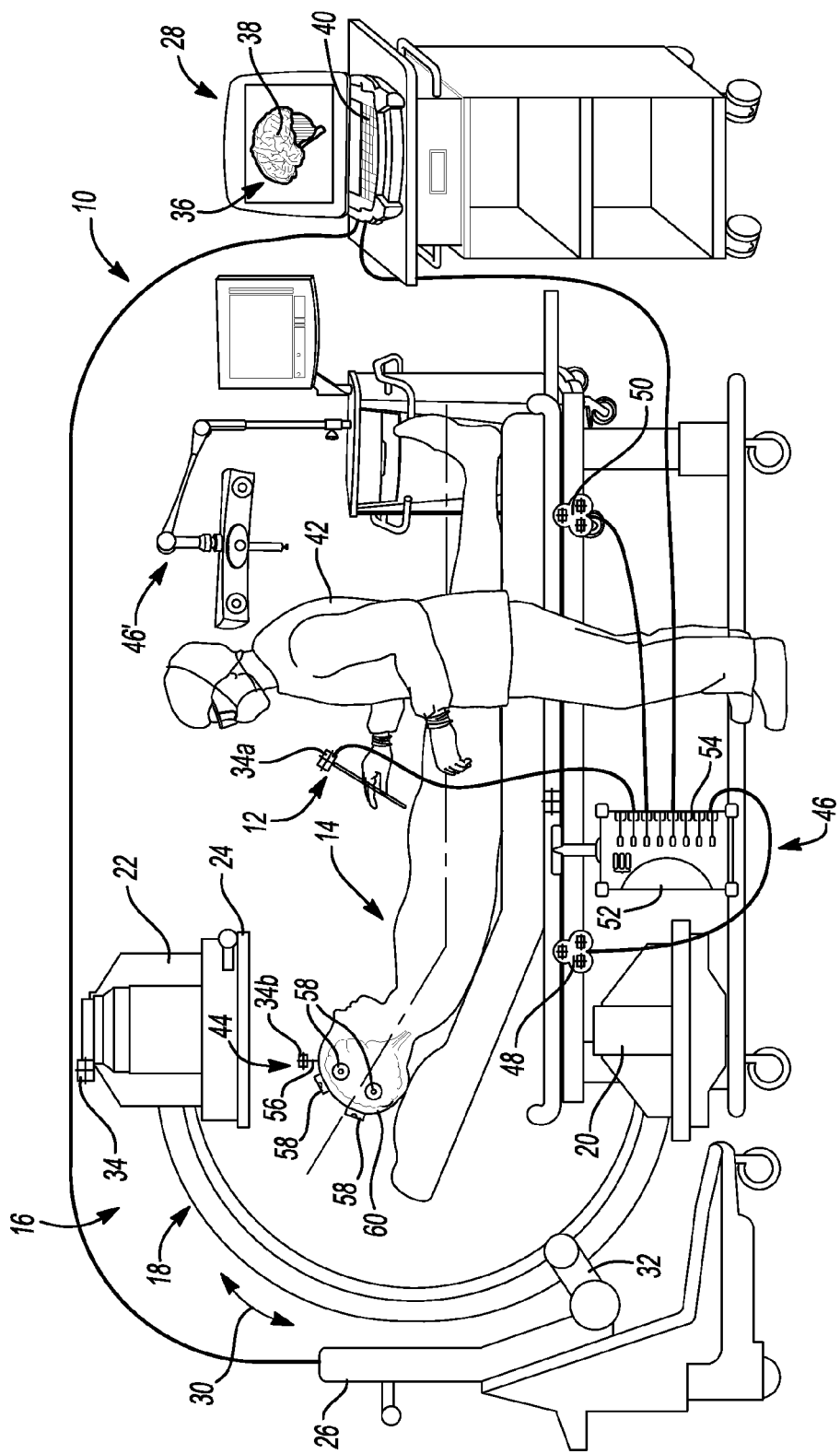
FIG. 1 is an environmental view of a surgical navigation system or computer aided surgical system, according to various embodiments.

With reference to FIG. 1, a navigation system 10 that can be used for various procedures is illustrated. The navigation system 10 can be used to track the location of a device 12, such as a pointer probe, relative to a patient 14 to assist in the implementation or performance of a surgical procedure. It should be further noted that the navigation system 10 may be used to navigate or track other devices including: catheters, probes, needles, leads, electrodes implants, etc. According to various embodiments, examples include ablation catheters, deep brain stimulation (DBS) leads or electrodes, microelectrode (ME) leads or electrodes for recording, etc. Moreover, the navigated device may be used in any region of the body. The navigation system 10 and the various devices may be used in any appropriate procedure, such as one that is generally minimally invasive, arthroscopic, percutaneous, stereotactic, or an open procedure. Although an exemplary navigation system 10 including an imaging system 16 are discussed herein, one skilled in the art will understand that the disclosure is merely for clarity of the present discussion and any appropriate imaging system, navigation system, patient specific data, and non-patient specific data can be used. For example, the intraoperative imaging system can include an MRI imaging system, such as the PoleStar® MRI imaging system or an O-arm® imaging system sold by Medtronic, Inc. having a place of business in Minnesota, USA. It will be understood that the navigation system 10 can incorporate or be used with any appropriate preoperatively or intraoperatively acquired image data.

The navigation system 10 can include the optional imaging device 16 that is used to acquire pre-, intra-, or post-operative, including real-time, image data of the patient 14. In addition, data from atlas models can be used to produce images for navigation, though they may not be patient images. Although, atlas models can be morphed or changed based upon patient specific information. Also, substantially imageless systems can be used, such as those disclosed in U.S. patent application Ser. No. 10/687,539, filed Oct. 16, 2003, now U.S. Pat. App. Pub. No. 2005/0085714, entitled "METHOD AND APPARATUS FOR SURGICAL NAVIGATION OF A MULTIPLE PIECE CONSTRUCT FOR IMPLANTATION", incorporated herein by reference. Various systems can use data based on determination of the position of various elements represented by geometric shapes.

The optional imaging device 16 is, for example, a fluoroscopic X-ray imaging device that may be configured as a C-arm 18 having an X-ray source 20, an X-ray receiving section 22, an optional calibration and tracking target 24 and optional radiation sensors. The calibration and tracking target 24 includes calibration markers (not illustrated). Image data may also be acquired using other imaging devices, such as those discussed above and herein.

An optional imaging device controller 26 may control the imaging device 16, such as the C-arm 18, which can capture the X-ray images received at the receiving section 22 and store the images for later use. The controller 26 may also be separate from the C-arm 18 and can be part of or incorporated into a work station 28. The controller 26 can control the rotation of the C-arm 18. For example, the C-arm 18 can move in the direction of arrow 30 or rotate about a longitudinal axis 14a of the patient 14, allowing anterior or lateral views of the patient 14 to be imaged. Each of these movements involves rotation about a mechanical axis 32 of the C-arm 18. The movements of the imaging device 16, such as the C-arm 18 can be tracked with a tracking device 34. As discussed herein, the tracking device, according to various embodiments, can be any appropriate tracking device to work with any appropriate tracking system (e.g. optical, electromagnetic, acoustic, etc.). Therefore, unless specifically discussed otherwise, the tracking device can be any appropriate tracking device.

In the example of FIG. 1, the longitudinal axis 14a of the patient 14 is substantially in line with the mechanical axis 32 of the C-arm 18. This enables the C-arm 18 to be rotated relative to the patient 14, allowing images of the patient 14 to be taken from multiple directions or in multiple planes. An example of a fluoroscopic C-arm X-ray device that may be used as the optional imaging device 16 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling mounted fluoroscopic systems, cath-lab fluoroscopic systems, fixed C-arm fluoroscopic systems, isocentric C-arm fluoroscopic systems, three-dimensional (3D) fluoroscopic systems, intraoperative O-arm™ imaging systems, etc.

The C-arm imaging system 18 can be any appropriate system, such as a digital or CCD camera, which are well understood in the art. Two dimensional fluoroscopic images that may be taken by the imaging device 16 are captured and stored in the C-arm controller 26. Multiple two-dimensional images taken by the imaging device 16 may also be captured and assembled to provide a larger view or image of a whole region of the patient 14, as opposed to being directed to only a portion of a region of the patient. For example, multiple image data or sets of data of a patient's leg, cranium, and brain may be appended together to provide a full view or complete set of image data of the leg or brain that can be later used to follow contrast agent, such as bolus or therapy tracking. The multiple image data can include multiple two-dimensional (2D) slices that are assembled into a 3D model or image.

The image data can then be forwarded from the C-arm controller 26 to the navigation computer and/or processor controller or work station 28 having a display device 36 to display image data 38 and a user interface 40. The work station 28 can also include or be connected to an image processor, a navigation processor, and a memory to hold instruction and data. The work station 28 can also include an optimization processor that assists in a navigated procedure. It will also be understood that the image data is not necessarily first retained in the controller 26, but may also be directly transmitted to the workstation 28. Moreover, processing for the navigation system and optimization can all be done with a single or multiple processors all of which may or may not be included in the workstation 28.

The work station 28 provides facilities for displaying the image data 38 as an image on the display device 36, saving, digitally manipulating, or printing a hard copy image of the received image data. The user interface 40, which may be a keyboard, mouse, touch pen, touch screen or other suitable device, allows a physician or user 42 to provide inputs to control the imaging device 16, via the C-arm controller 26, or adjust the display settings of the display 36. The work station 28 may also direct the C-arm controller 26 to adjust the rotational axis 32 of the C-arm 18 to obtain various two-dimensional images in different planes in order to generate representative two-dimensional and three-dimensional images.

While the optional imaging device 16 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), positron emission tomography (PET), optical coherence tomography (OCT) (a more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference). Intra-vascular ultrasound (IVUS), intra-operative CT, single photo emission computed tomography (SPECT), planar gamma scintigraphy (PGS). Addition imaging systems include intraoperative MRI systems such as the PoleStar® MRI imaging system. Further systems include the O-Arm® imaging system. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 14. It should further be noted that the optional imaging device 16, as shown in FIG. 1, provides a virtual bi-plane image using a single-head C-arm fluoroscope as the optional imaging device 16 by simply rotating the C-arm 18 about at least two planes, which could be orthogonal planes to generate two-dimensional images that can be converted to three-dimensional volumetric images. By acquiring image data in more than one plane, an icon representing the location of an impacter, stylet, reamer driver, taps, drill, DBS electrodes, ME electrodes for recording, probe, or other instrument, introduced and advanced in the patient 14, may be superimposed in more than one view on display 36 allowing simulated bi-plane or even multi-plane views, including two and three-dimensional views.

Four-dimensional (4D) image information can be used with the navigation system 10 as well. For example, the user 42 can use a physiologic signal, which can include Heart Rate (measured with an EKG), Breath Rate (Breath Gating) and combine this data with image data 38 acquired during the phases of the physiologic signal to represent the anatomy of the patient 14 at various stages of the physiologic cycle. For example, with each heartbeat the brain pulses (and therefore moves). Images can be acquired to create a 4D map of the brain, onto which atlas data and representations of a device, such as a surgical instrument can be projected. This 4D data set can be matched and co-registered with the physiologic signal (e.g. EKG) to represent a compensated image within the system. The image data registered with the 4D information can show the brain (or anatomy of interest) moving during the cardiac or breath cycle. This movement can be displayed on the display 36 as the image data 38. Also, the gating techniques can be used to eliminate movement in the image displayed on the display device 36.

Likewise, other imaging modalities can be used to gather the 4D dataset to which pre-operative 2D and 3D data can be matched. One need not necessarily acquire multiple 2D or 3D images during the physiologic cycle of interest (breath or heart beat). Ultrasound imaging or other 4D imaging modalities can be used to create an image data that allows for a singular static pre-operative image to be matched via image-fusion techniques and/or matching algorithms that are non-linear to match the distortion of anatomy based on the movements during the physiologic cycle. The combination of a dynamic reference frame 44 and 4D registration techniques can help compensate for anatomic distortions during movements of the anatomy associated with normal physiologic processes.

With continuing reference to FIG. 1, the navigation system 10 can further include a tracking system, such as, but not limited to, an electromagnetic (EM) tracking system 46 or an optical tracking system 46'. Either or both can be used alone or together in the navigation system 10. Moreover, discussion of the EM tracking system 46 can be understood to relate to any appropriate tracking system. The optical tracking system 46' can include the Stealthstation® Treatment Guidance System including the Treon® Navigation System and the Tria® Navigation System, both sold by Medtronic Navigation, Inc. Other tracking systems include acoustic, radiation, radar, infrared, etc.

The EM tracking system 46 includes a localizer, such as a coil array 48 and/or second coil array 50, a coil array controller 52, a navigation probe interface 54, a device 12 (e.g. catheter, needle, pointer probe, or instruments, as discussed herein) and the dynamic reference frame 44. An instrument tracking device 34*a* can also be associated with, such as fixed to, the instrument 12 or a guiding device for an instrument. The dynamic reference frame 44 can include a dynamic reference frame holder 56 and a removable tracking device 34b. Alternatively, the dynamic reference frame 44 can include the tracking device 34b that can be formed integrally or separately from the DRF holder 56.

Moreover, the DRF 44 can be provided as separate pieces and can be positioned at any appropriate position on the anatomy. For example, the tracking device 34b of the DRF can be fixed to the skin of the patient 14 with an adhesive. Also, the DRF 44 can be positioned near a leg, arm, etc. of the patient 14. Thus, the DRF 44 does not need to be provided with a head frame or require any specific base or holding portion.

The tracking devices 34, 34a, 34b or any tracking device as discussed herein, can include a sensor, a transmitter, or combinations thereof. Further, the tracking devices can be wired or wireless to provide a signal emitter or receiver within the navigation system. For example, the tracking device can include an electromagnetic coil to sense a field produced by the localizing array 48, 50 or reflectors that can reflect a signal to be received by the optical tracking system 46'. Nevertheless, one will understand that the tracking device can receive a signal, transmit a signal, or combinations thereof to provide information to the navigation system 10 to determine a location of the tracking device 34, 34a, 34b. The navigation system 10 can then determine a position of the instrument or tracking device to allow for navigation relative to the patient and patient space.

The coil arrays 48, 50 may also be supplemented or replaced with a mobile localizer. The mobile localizer may be one such as that described in U.S. patent application Ser. No. 10/941,782, filed Sep. 15, 2004, now U.S. Pat. App. Pub. No. 2005/0085720, entitled "METHOD AND APPARATUS FOR SURGICAL NAVIGATION", herein incorporated by reference. As is understood the localizer array can transmit signals that are received by the tracking devices 34, 34a, 34b. The tracking devices 34, 34a, 34b can then transmit or receive signals based upon the transmitted or received signals from or to the array 48, 50.

Further included in the navigation system 10 may be an isolator circuit or assembly (not illustrated separately). The isolator circuit or assembly may be included in a transmission line to interrupt a line carrying a signal or a voltage to the navigation probe interface 54. Alternatively, the isolator circuit included in the isolator box may be included in the navigation probe interface 80, the device 12, the dynamic reference frame 44, the transmission lines coupling the devices, or any other appropriate location. The isolator assembly is operable to isolate any of the instruments or patient coincidence instruments or portions that are in contact with the patient should an undesirable electrical surge or voltage take place.

It should further be noted that the entire tracking system 46, 46' or parts of the tracking system 46, 46' may be incorporated into the imaging device 16, including the work station 28. Incorporating the tracking system 46, 46' may provide an integrated imaging and tracking system. This can be particularly useful in creating a fiducial-less system. Moreover, fiducial marker-less systems can include a tracking device and a contour determining system, including those discussed herein. Any combination of these components may also be incorporated into the imaging system 16, which again can include a fluoroscopic C-arm imaging device or any other appropriate imaging device.

The EM tracking system 46 uses the coil arrays 48, 50 to create an electromagnetic field used for navigation. The coil arrays 48, 50 can include a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil array 48 is controlled or driven by the coil array controller 52. The coil array controller 52 drives each coil in the coil array 48 in a time division multiplex or a frequency division multiplex manner. In this regard, each coil may be driven separately at a distinct time or all of the coils may be driven simultaneously with each being driven by a different frequency.

Upon driving the coils in the coil array 48 with the coil array controller 52, electromagnetic fields are generated within the patient 14 in the area where the medical procedure is being performed, which is again sometimes referred to as patient space. The electromagnetic fields generated in the patient space induce currents in the tracking device 34, 34a, 34b positioned on or in the device 12, DRF 44, etc. These induced signals from the tracking devices 34, 34a, 34b are delivered to the navigation probe interface 54 and subsequently forwarded to the coil array controller 52. The navigation probe interface 54 can also include amplifiers, filters and buffers to directly interface with the tracking device 34b attached to the device 12. Alternatively, the tracking device 34b, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 54.

Various portions of the navigation system 10, such as the device 12, the dynamic reference frame 44, are equipped with at least one, and generally multiple, EM or other tracking devices 34a, 34b, that may also be referred to as localization sensors. The EM tracking devices 34a, 34b can include one or more coils that are operable with the EM localizer arrays 48, 50. An alternative tracking device may include an optical device, and may be used in addition to or in place of the electromagnetic tracking devices 34a, 34b. The optical tacking device may work with the optional optical tracking system 46'. One skilled in the art will understand, however, that any appropriate tracking device can be used in the navigation system 10. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

In brief, the EM tracking device 34a on the device 12 can be in a handle or inserter that interconnects with an attachment and may assist in placing an implant or in driving a member. The device 12 can include a graspable or manipulable portion at a proximal end and the tracking device 34b may be fixed near the manipulable portion of the device 12 or at a distal working end, as discussed herein. The tracking device 34a can include an electromagnetic tracking sensor to sense the electromagnetic field generated by the coil array 48, 50 that can induce a current in the electromagnetic device 34a. Alternatively, the tracking device 34a can be driven (i.e., like the coil array above) and the tracking array 48, 50 can receive a signal produced by the tracking device 34a.

The dynamic reference frame 44 may be fixed to the patient 14 adjacent to the region being navigated so that any movement of the patient 14 is detected as relative motion between the coil array 48, 50 and the dynamic reference frame 44. The dynamic reference frame 44 can be interconnected with the patient in any appropriate manner, including those discussed herein. Relative motion is forwarded to the coil array controller 52, which updates registration correlation and maintains accurate navigation, further discussed herein. The dynamic reference frame 44 may include any appropriate tracking device. Therefore, the dynamic reference frame 44 may also be EM, optical, acoustic, etc. If the dynamic reference frame 44 is electromagnetic it can be configured as a pair of orthogonally oriented coils, each having the same center or may be configured in any other non-coaxial or co-axial coil configurations.

Briefly, the navigation system 10 operates as follows. The navigation system 10 creates a translation map between all points in the image data generated from the imaging device 16 which can include external and internal portions, and the corresponding points in the patient's anatomy in patient space. After this map is established, whenever the tracked device 12 is used, the work station 36 in combination with the coil array controller 52 uses the translation map to identify the corresponding point on the image data or atlas model, which is displayed on display 36. This identification is known as navigation or localization. An icon representing the localized point or instruments is shown on the display 36 within several two-dimensional image planes, as well as on three and four dimensional images and models.

To enable navigation, the navigation system 10 must be able to detect both the position of the patient's anatomy and the position of the instrument 12 or an attachment member (e.g. tracking device 34a) attached to the instrument 12. Knowing the location of these two items allows the navigation system 10 to compute and display the position of the instrument 12 or any portion thereof in relation to the patient 14. The tracking system 46 is employed to track the instrument 12 and the anatomy of the patient 14 simultaneously.

The tracking system 46, if it is using an electromagnetic tracking assembly, essentially works by positioning the coil array 48, 50 adjacent to the patient 14 to generate a magnetic field, which can be low energy, and generally referred to as a navigation field. Because every point in the navigation field or patient space is associated with a unique field strength, the electromagnetic tracking system 46 can determine the position of the instrument 12 by measuring the field strength at the tracking device 34a location. The dynamic reference frame 44 is fixed to the patient 14 to identify the location of the patient in the navigation field. The electromagnetic tracking system 46 continuously computes or calculates the relative position of the dynamic reference frame 44 and the instrument 12 during localization and relates this spatial information to patient registration data to enable navigation of the device 12 within and/or relative to the patient 14. Navigation can include image guidance or imageless guidance.

Patient registration is the process of determining how to correlate the position of the instrument 12 relative to the patient 14 to the position on the diagnostic or image data. To register the patient 14, the physician or user 42 may select and store one or more particular points from the image data and then determine corresponding points on the patient's anatomy, such as with the pointer probe 12. The navigation system 10 analyzes the relationship between the two sets of points that are selected and computes a match, which correlates every point in the image data with its corresponding point on the patient's anatomy or the patient space.

The points that are selected to perform registration can be image fiducial points. The image fiducial points can be produced by a fiducial marker 58 or selected landmarks, such as anatomical landmarks. The landmarks or fiducial markers 58 are identifiable in the image data and identifiable and accessible on the patient 14. The anatomical landmarks can include individual or distinct points on the patient 14 or contours (e.g. three-dimensional contours) defined by the patient 14. The fiducial markers 58 can be artificial markers that are positioned on the patient 14. The artificial landmarks, such as the fiducial markers 58, can also form part of the dynamic reference frame 44, such as those disclosed in U.S. Pat. No. 6,381,485, entitled "Registration of Human Anatomy Integrated for Electromagnetic Localization," issued Apr. 30, 2002, herein incorporated by reference. Various fiducial marker-less systems, including those discussed herein, may not include the fiducial markers 58, or other artificial markers. The fiducial marker-less systems include a device or system to define in the physical space the landmark or fiducial points on the patient or contour on the patient. A fiducialless and markerless system can include those that do not include artificial or separate fiducial markers that are attached to or positioned on the patient 14.

As discussed above, registration of the patient space or physical space to the image data or image space can require the correlation or matching of physical or virtual fiducial points and image fiducial points. The physical fiducial points can be the fiducial markers 60 or landmarks (e.g. anatomical landmarks) in the substantially fiducial marker-less systems.

The registration can require the determination of the position of physical fiducial points. The physical fiducial points can include the fiducial markers 58. The user 42 can touch the fiducial markers or devices 58 on the patient 14 or a tracking device can be associated with the fiducial markers 58 so that the tracking system 46, 46' can determine the location of the fiducial markers 58 without a separate tracked device. The physical fiducial points can also include a determined contour (e.g. a physical space 3d contour) using various techniques, as discussed herein.

The image fiducial points in the image data 54 can also be determined. The user 42 can touch or locate the image fiducial points, either produced by imaging of the fiducial markers 48 or the landmarks. Also, various algorithms are generally known to determine the location of the image fiducial points. The image fiducial points can be produced in the image data by the fiducial markers 48, particular landmarks, or a contour (e.g. a 3D contour) of the patient 14 during acquisition of the image data.

Once the physical fiducial points and the image fiducial points have been identified, the image space and the physical space can be registered. A processor, such as a processor within the workstation 28, can determine registration of the patient space to the image space. The registration can be performed according to generally known mapping or translation techniques. The registration can allow a navigated procedure using the image data.

Figure 2:
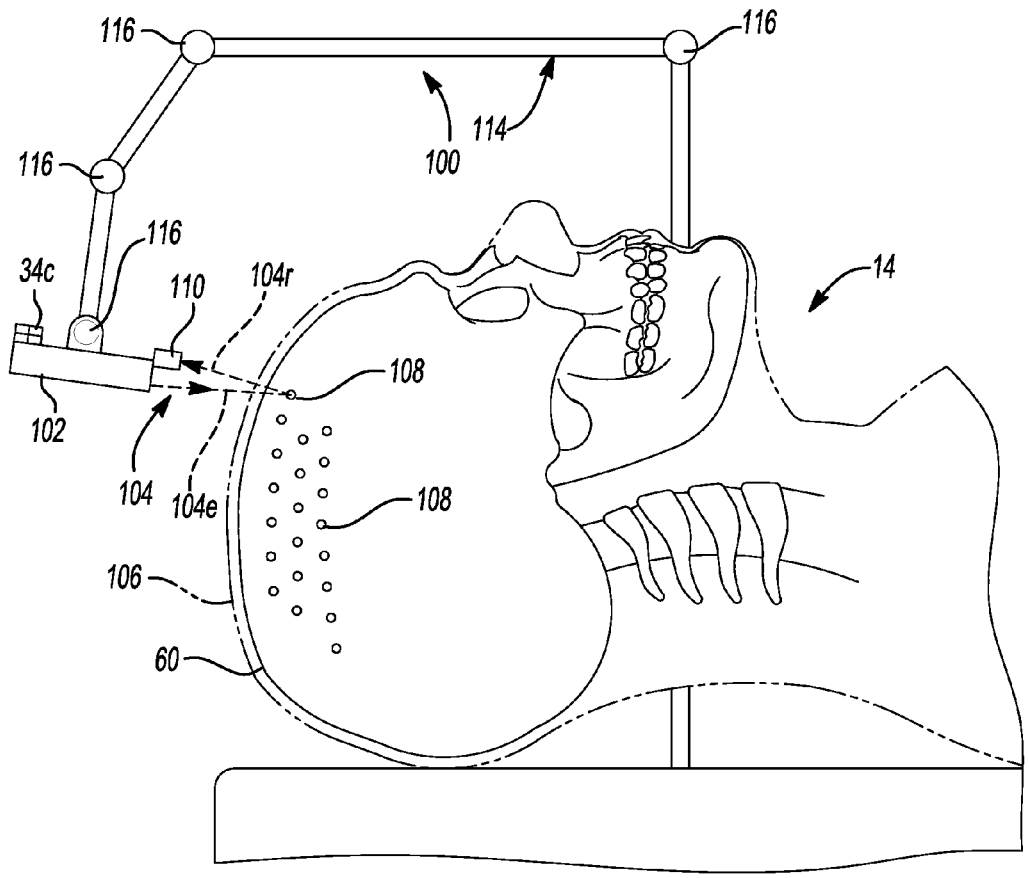
FIG. 2 is a detailed environmental view of a skin penetrating laser system.

According to various embodiments, a fiducial marker-less system can use a soft tissue penetrating or bone position determining laser system 100, as illustrated in FIG. 2. The skin penetrating laser system 100 can include a laser generator 102 that can direct a laser beam 104 to reflect off a bone structure, such as the cranium or skull 60 by penetrating through soft tissue 106, including dermis, circulatory tissues, muscle, vasculature, and the like. Although the current discussion relates to a procedure near the cranium 60, a procedure can also occur near other anatomical portions of the patient 14. Thus, the laser beam 104 may be required to pass through more or less soft tissue than near the cranium 60. For example, a great amount or mass of muscle tissue may be present near a spinal column, femur, etc. One skilled in the art will understand that the amount and type of soft tissue to penetrate can also require the laser beam 104 to be of an appropriate power, wavelength, etc. that can differ depending upon the amount and type of soft tissue to penetrate.

The laser beam 104 can include an emission beam 104e and a reflection beam 104r. The emission beam 104e can impact or contact the bone structure, including the cranium 60, at a point or virtual physical fiducial point 108. The reflection beam 104r can then reflect, according to generally understood physical requirements, to a receiver, such as a receiver 110 associated with the laser device 102. The reflection occurs at a point or reflection point which can be the virtual physical fiducial point 108. The reflection point can be interpreted or determined to be the virtual physical fiducial point 108 for purposes of correlation or registration, as discussed further here.

A receiver 110 can receive the reflected beam 104r from the virtual physical fiducial point 108 and determine a distance of the virtual physical fiducial point 108 from the laser device 102. Determining a distance from the receiver to the virtual physical fiducial point 108 can be determined using various techniques. For example, a pulsed beam may be used and a time of transmission can be determined or a variance in phase can be used to determine distance traveled. Determining a distance with a laser beam, however, is generally understood by those skilled in the relevant art.

A position of the laser device 102 or the receiver 110 can be determined, according to various embodiments. For example, the position of the laser device 102 or the receiver 110 can be tracked with the tracking device 34a. The tracking device 34a can be tracked with the tracking system 46, as discussed above. This allows the navigation system 10 to determine the position of the virtual physical fiducial point 108 in the patient space.

The virtual physical fiducial point 108 can be manually or automatically correlated to a point in the image data 38. According to various embodiments, however, the laser device 102 can be moved to a plurality of positions relative to the patient 14 and the cranium 60. By moving the laser device 102 relative to the patient 14, a plurality of the virtual points 108 can be determined in the patient space. The laser device 102 can also be moved over relative to the patient 14 and a plurality of the physical fiducial points 108 can be determined while the laser device 102 is moved. Thus, one will understand, that the laser device 102 need not be moved to discrete points, but can be moved in a pattern relative to the patient 14 and the points can be collected while it is moved.

Once a selected number of virtual points 108 are created or determined the processor, such as in the workstation 28, can match a contour determined via the physical fiducial points 108 and a contour determined in the image data 54. As discussed above, various techniques are known to determine contours based on the determined physical fiducial points 108 or in the image data. Examples include, edge detection, region growing, etc. Also, the contours, as discussed throughout, can include 2D or 3D contours, depending upon the amount of points or location of points and the type of image data. Systems that can be used to obtain contour information or provide enough points to determine a contour in physical space, as discussed above, can also be referred to contour determining systems.

The contour of the patient 14 can be determined by determining the plurality of the fiducial points 108 on the patient 14 with the laser device 102. Various algorithms can also be used to determine a contour of the patient 14 with a plurality of the virtual physical fiducial points 108, prior to determining a match to contours in the image data. For example, the physical fiducial points 108 can be related to one another define a line or 3D contour of the patient 14 that can be correlated to a contour determined in the image data 38. One skilled in the art will understand that the various distinct points can also be used to perform the registration, thus the 3D contour as the fiducial points is merely exemplary.

The laser device 102 can be interconnected to a stand or manipulation arm 114 that can include one or more moveable joints 116. The moveable joints 116 can be robotically manipulated or controlled, such as with the workstation 28. Alternatively, the moveable joints 116 can be moved by a user, such as the user 42. A tracking device 34c can be used to determine the position of the laser device 102 in the physical space to compare or register the image data to the physical space. The position of the laser device 102 can also be determined via a position algorithm, if the stand mechanism 114 is robotically controlled or includes various movement or position determination devices, such as potentiometers, stepper motors, or the like.

The laser device 102, which can have the tracking device 34c associated therewith, can be the device 12. As illustrated in FIG. 1, the device 12 can be independently held by the user 42 and can be moved relative to the patient 14. Thus, the laser device 102 can also be held by the user 42, free of the stand 114, and moved relative to the patient 14 to determine a line, 3D contour, or any selected number of distinct physical fiducial points 108.

The laser device 102 can be any appropriate laser device. The laser device 102 can produce the beam 104 that is operable to substantially pass through soft tissue surrounding a substantially rigid structure, such as a bone structure including a cranium 60, and reflect off the rigid structure. The laser device 102 can emit any appropriate laser beam, such as one that includes a wave length of about 750 nanometers to about 810 nanometers.

The rigid structure of the bone, including the cranium 60, can be effectively used to register image space to the physical space. The structure of the bone rarely changes shape or configuration between the time of the acquisition of the image data and the determination of the virtual points 108, either during or immediately preceding a surgical procedure. The bone structure, therefore, can provide an appropriate structure for comparison between the physical space and the image space.

The physical fiducial points 108 can be located on the patient 14 according to various embodiments. For example, the patient 14, including the cranium 60, can be fixed in the physical space. Thus, the physical fiducial points 108 are fixed in physical space once they are determined. Also, a DRF, such as the DRF 44, can be interconnected with the patient 14. When the DRF 44 is attached, the patient 14 can move and the physical fiducial points 108 can still be related to one another within the physical space and the navigation system 10 because of the DRF 44 tracking the movement of the patient 14.

A receiver or sensor 110 can receive the reflected beam 104r to determine the position of the point 108. The processor, such as the processor on the workstation 28, can determine the distance between the laser device 102 or the tracking device 34c to determine the position of the virtual fiducial point 108. The determination of a distance based upon a reflected laser beam is well understood in the art.

As discussed above, matching or correlating of a contour in the physical space and a contour in the image space can be used to register the image space and the physical space. The physical space, including the patient space, can have a contour defined by one or more of the fiducial points 108. The contour can also be referred to as a fiducial point alone. This can allow the laser system 100 to act or perform a contour determination or act as a contour forming system. A contour can also be defined in the image data in the image space, using generally known techniques and algorithms that can be performed by the processor. Further, the contours from the image space can then be matched to the contours in the physical space to perform a registration of the image space to the physical space.

The registered image space to the physical space can then be used in a surgical navigation procedure, such as the placement of a micro-electrode or deep brain stimulation electrode in the cranium 60. As discussed above the various physical fiducial points 108 can be determined and, if desired, a contour can be determined from a plurality of the physical fiducial points 108. The contour or the plurality of the physical fiducial points can be used to match or correlate to the image space. The image data can then be used to navigate the selected procedure.

A registration can be performed without the fiducial markers 58 using the laser system 100. The laser system 100, however, is a contour determination system or fiducial marker-less registration system, according to various embodiments. Contour determination systems or fiducial marker-less registration systems can also include various tracked portions, as discussed herein.

Figure 3:
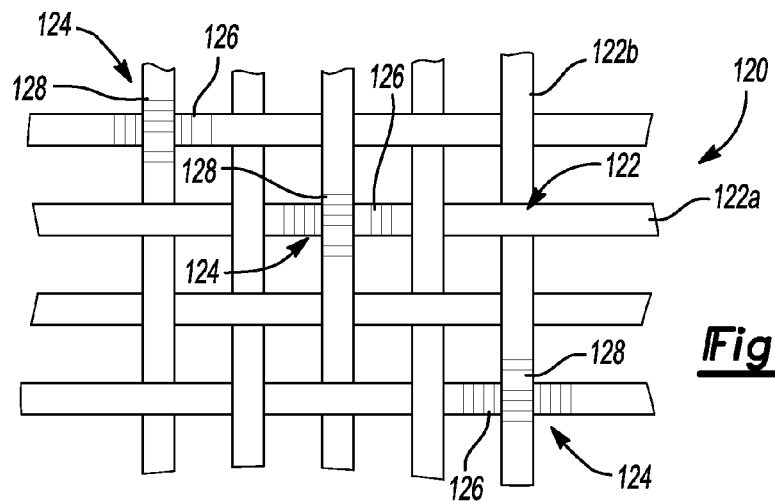
FIG. 3 is a detailed view of a flexible member including tracking devices, according to various embodiments.

According to various embodiments, with reference to FIG. 3, a flexible sheet or member 120 can include one or more fibers 122. The fibers 122 can include woven fibers, for illustration purposes only, that include longitudinal fibers 122a and latitudinal fibers 122b. Nevertheless, the fibers can be woven into any appropriate material, such as a sheet, a drape, and the like. Moreover, the member 120 can be sized with any appropriate dimensions, such as to cover a selected portion of the anatomy.

The fibers 122 of the member 120 can have a tracking device 124 formed around them or relative to them. According to various embodiments, the tracking device 124 can include a first coil member 126 and a second coil member 128. The two coil members 126, 128 can be substantially perpendicular to one another and be used with the tracking system 46 and can be similar to the tracking devices 34. The sheet 120 can include a plurality of the tracking devices 124 that can be positioned at selected points, such as about one millimeter apart, two millimeters apart, one centimeter apart, or any appropriate dimension. As discussed above, the tracking devices 124 can, according to various embodiments, sense a strength of a field, such as an electromagnetic field, produced by the localizer device 48. Therefore, the sheet 120 including the plurality of the tracking devices 124 can provide a plurality of tracked positions relative to whatever the sheet 120 is placed over. As discussed above, the tracking devices can be tracked relative to the patient 14.

It will be understood that the tracking devices 124 that can be associated with the sheet 120 can be any appropriate type of tracking device. For example, optical tracking devices, including active optical or passive optical members, can be used as tracking devices with the tracking system 46'. The active optical members, including light emitting diodes (LEDs) can be associated with the sheet 120. Similarly, passive optical members, including reflectors, can be associated with the sheet 120. The tracking devices 124 can either emit or reflect optical wavelengths to the optical tracking system 46' and the position of the optical tracking devices can be tracked, as is generally understood in the art. Thus, one skilled in the art will understand, any appropriate tracking system can be used and any appropriate tracking device can be associated with the sheet.

The sheet 120, as mentioned briefly above, can be dimensioned to be positioned on the patient 14. For example the sheet 120 can cover an expanse and be placed to cover an exterior portion of the patient 14. The sheet 120 can also be provided to maintain a sterile field relative to the patient 14. The sheet 120 can, generally, include a top and bottom surface covering an expanse and a relatively thin edge. The sheet 120 can be substantially flexible to drape over and conform to a selected portion of the patient 14.

As discussed herein, the plurality of tracked points can provide information relating to the position of each of the tracking devices 124 on the patient 14. The information can be used for tracking the patient 14, determining the contour of the patient 14, registering image space to patient space, or the like.

The sheet 120 can be sized or dimensioned to cover any appropriate portion of the patient 14. For example, a large single sheet can be formed to cover a portion of the cranium 60 (FIG. 5). Also, a long narrow sheet can be formed to wrap around a selected anatomical portion. In any case, the plurality of the tracking devices 124 or selected tracking device can be used to provide position information at a plurality of points on the patient 14.

The plurality of the points can be physical fiducial points. The physical fiducial points can be similar to the physical fiducial points 108 and can be used alone or to define a physical space 3D contour. The physical space contour or fiducial point can be correlated to a 3D contour or image data fiducial point. Thus, providing the plurality of the tracking devices in the sheet to provide position information at a plurality of points can provide information similar to the physical fiducial points 108.

According to various embodiments, a 3D contour can be determined based upon the tracking devices associated with the sheet 120. The contour can be compared to and matched to a contour in the image data. Alternatively, or in addition thereto, the sheet 120 and the tracking devices can be used as fiducial points and can be imaged with the patient 14. Thus, the tracking devices, or portions associated therewith, can be imaged and produce image fiducial points to be correlated to physical space fiducial points.

According to various embodiments, a flexible member or sheet 140, with reference to FIG. 4, can be provided of a substantially continuous material. For example, the sheet 140 can be formed of a polymer or other substantially non-porous material. The sheet 140 can include the Steri-Drape® surgical drapes sold by 3M Company Corporation of St. Paul, Minn. The surgical drapes allow for maintaining a sterile field around a selected portion of the patient 14. The sheet 140, as mentioned briefly above, can be dimensioned to be positioned on the patient 14. For example the sheet 140 can cover an expanse and be placed to cover an exterior portion of the patient 14. The sheet 140 can also be provided to maintain a sterile field relative to the patient 14. The sheet 140 can, generally, include a top and bottom surface covering an expanse and a relatively thin edge. The sheet 140 can be substantially flexible to drape over and conform to a selected portion of the patient 14.

The sheet 140 can be pierced or cut for access to a particular location, such as a position on the cranium 60 of the patient 14. The sheet 140 can also include a flap 142 that can be moved or removed to gain access through a portal 144 to a selected region of the cranium 60.

The sheet 140 can include a tracking device 146 or a plurality of the tracking devices 146. The tracking devices 146 can be positioned in the sheet 140 in any appropriate manner. For example, the tracking devices 146 can be positioned within the sheet 140 in a substantially grid or aligned manner. The tracking devices 146 can be positioned with regular spacing from one another to provide for a plurality of trackable points or positions, similar to the coil pairs 124, 126 of the sheet 120.

The tracking devices 146 can also include optical tracking devices, as discussed above. The optical tracking devices can be active or passive tracking devices. The optical tracking devices can work with the optical tracking system 46' to provide position information of the patient 14. Also, the sheet 140 can be placed on the patient 14 while image data is being acquired of the patient 14. Thus, the sheet 140 can also be used to produce image fiducial points, as discussed above.

With reference to FIGS. 3 and 4 and additional reference to FIG. 5, the exemplary sheet 140 can be draped over the patient 14, such as over the cranium 60. The sheets 120, 140, according to various embodiments can include a selected flexibility or stiffness. The sheets 120, 140, can be flexible enough to substantially conform to a surface contour of the patient 14. Also, the sheets 120, 140 can be light enough to be placed on the patient 14 without substantially deforming the soft tissue around the boney structure. Thus, the determined contour of the patient 14 with the sheets 120, 140 can be substantially similar to a contour of a surface of the patient 14 with no covering.

Also, as discussed above, the sheets 120, 140 can be used to maintain a sterility relative to the patient 14. The sheets 120, 140 can cover or define an expanse. The sheets 120, 140 can be provided to be draped over or conform to a selected portion, such as an exterior surface, of the patient 14

The tracking devices 146 associate with the sheet 140 can be flexible or of an appropriate dimension to be positioned over the cranium 60 in a substantially close manner. As discussed above, the sheet 140 can be substantially similar to surgical sterile sheets so that the sheet 140 can substantially match the outer contour of the dermis or skin of the patient 14 by being substantially in contact with the surface of the patient 14.

The sheet, such as the sheet 140 can also include various modular or openable portions 144. The open or flap portion 144 can allow for access to various portions of the anatomy of the patient 14 without removal or separately cutting through the sheet 140. The tracking devices 146 can be positioned near or around the flap portion 144 to allow for substantially precise determination location of an area around the flap portion 144. Further, the sheet 140 can be positioned to cover a selected portion of the anatomy or cling to a selected portion of the anatomy to precisely define or substantially precisely position the coils 124,126 or the tracking devices 146 at selected locations relative to the patient 14.

The sheets 140, 120 can also include a selected weight or mass that does not does substantially compress or deform the soft tissue of the patient 14. For example, a fiducial marker or trackable device can be interconnected with the patient 14 that deforms soft tissue surrounding bone of the patient 14. The deformation of the soft tissue with the tracking device or while positioning the tracking device can introduce certain inaccuracies into the navigation or tracking system 46. Thus, the sheets 120, 140 can be provided with an appropriate mass, density, mass evenness, and the like to substantially remove or eliminate the possibility of an unwanted or undesired deformation. Although a deformation can be accounted for in a tracking system or a navigation system 10, removing the possibility of such deformation can assist in the efficiency of the navigation system 10.

The sheets 120. 140. can also be formed to include a selected shape or 3D contour. For example, the sheets 120, 140 can be formed to include a shape that substantially matches a portion of the patient's 14 anatomy, including the cranium 60. Thus, the sheets 120, 140 can be efficiently positioned in a selected location. Also, the sheets 120, 140 can be preformed and flexible for a substantially custom or unique fit to the patient 14.

Further, the tracking devices 146 positioned within the sheet 140 can also then substantially contact the skin or be positioned relative to the skin to provide position information in concert with the tracking system 46. As discussed above, the tracking devices 146 can be tracked with the tracking system 46 to determine the position relative to the patient 14. The coils 124, 126 in the sheet 120 can be formed to contact the skin or surface of the patient 14 as well.

The tracking devices 146 can include any appropriate dimension, which can be substantially identical to a thickness of the sheet 140. Therefore, the tracking devices 146 can substantially contact the skin of the patient 14, relative to which the sheet 140 is positioned. In addition, the tracking devices 146 can include a selected dimension to position within the sheet 140 at a selected depth or orientation. Also, the coil pairs 124, 126 in the sheet 120 can substantially contact the surface on which the sheet 120 is positioned by the configuration of coils 124, 126 on the fibers 122. According to various embodiments, the coils 124, 126 or the tracking devices 146 can be configured in the respective sheets 120, 140 to contact the skin of the patient 14 for selected accuracy.

The tracking devices 146 and the coil pairs 124, 126 can be wired, wireless, or any appropriate configuration to transfer information to the tracking system 46 to allow a determination of the location or position of the tracking devices 140 and coils 124, 126. The positioning of the plurality of tracking devices 140 relative to the patient 14 can allow for a plurality of data point or patient points to be tracked by the tracking system 46. The plurality of points can effectively define a contour or surface of the patient 14. The contour can be a 2D or 3D contour of the patient 14.

As discussed above, certain contour matching algorithms can be used to register patient space to image space. By tracking the plurality of the positions of the tracking devices 146 or the coils 124, 126 can provide the contour information that can be matched or registered to contours represented in the image data. Therefore, the sheets 120, 140 can be provided to allow for registration of the patient space to the image space. The sheets 140, 120 can also be provided for various purposes such as covering the patient, providing a sterile field in an operating room, or other purposes.

Thus, the sheets 120, 140 can be placed on the patient 14 and the tracking devices in the sheets can be tracked to determine one or more physical fiducial points. A plurality of the determined fiducial points can be used to define a contour of the patient 14. The contour of the patient 14 can then be matched to a contour that is determined in the image data, as discussed above. The matching of the contours can be used to register the image space to the physical space. The registered image data can be used in a navigated procedure.

As discussed above, the navigation system 10 can be used to navigate various instruments relative to the patient 14, such as a catheter, a lead (e.g. a DBS, or micro-electrode lead), or the like into the cranium 60. The various devices, including the laser system 100, the sheets 120, 140 and the like, can be used to provide information within the navigation system 10 to allow a determination of a registration between the image space and the patient space. Various other systems can also be used to perform a registration of image space to physical space without fiducial markers 58. For example, the Tracer™ sold by Medtronic Inc. can include an instrument that can be positioned at several points or drawn across a skin surface and tracked within the tracking system 46 to determine a contour of a skin surface. Similarly, the Fazer® Contour Laser System sold by Medtronic, Inc. can be used to determine or scan across a skin surface to determine a skin surface for registration. The determined skin surface can then be matched or used to register the image space to the patient space.

According to various embodiments, a contour determining device or system (e.g. the laser system 100, sheets 120, 140, the Fazer™ Contour Laser System, etc.) can be used to locate or determine various points on the patient 14. The points can be fiducial points that include a single point or a contour (i.e. 2D or 3D). Moreover, the various contour determining devices can be tracked with the tracking systems 46, 46'. The position of the contour determining devise can be processor or determined in a processor in the tracking system alone or in the works station alone 28, or combinations thereof. Also, the information collected with the tracking system 46, 46' can be transferred to any appropriate processor for position determination. According to various embodiments, a separate processor or the same processor can also perform the registration of he image space to patient space and determine the position of the tracked instrument relative to the image data.

Figure 6:
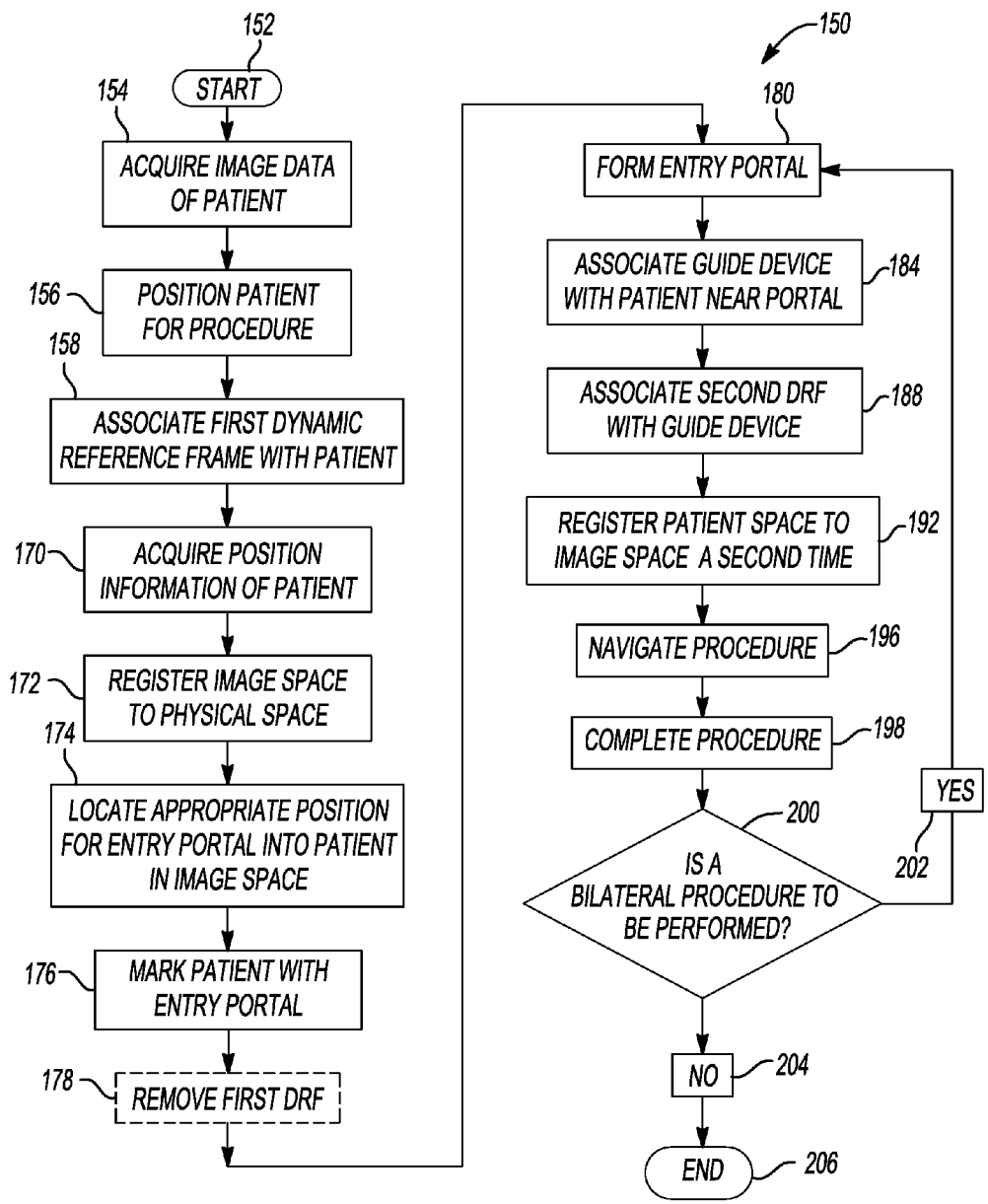
FIG. 6 is a flow chart of a process for performing a selected procedure.
Figure 7:
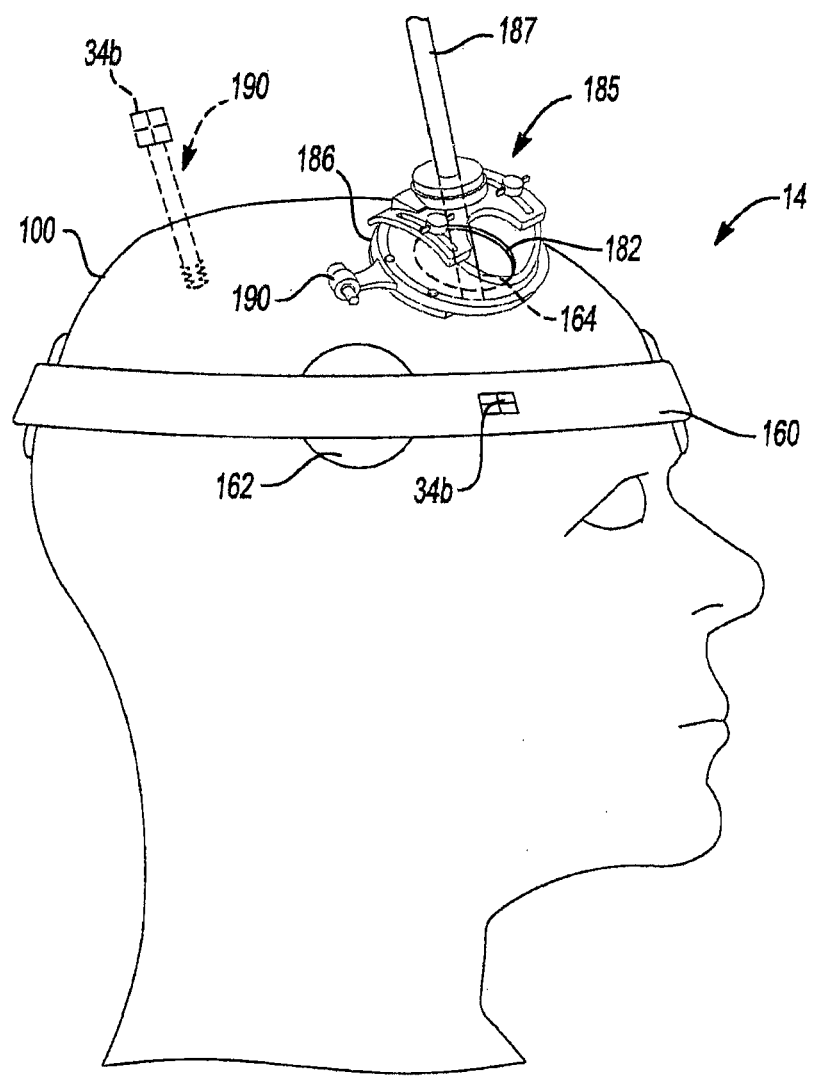
FIG. 7 is an environmental view of a patient including various elements associated therewith.

According to various embodiments, with reference to FIG. 6, a navigation system, such as a navigation system 10, can be used to perform a procedure according to various processes. A method of performing a registration and surgical procedure 150 is illustrated, which can use the navigation system 10. In the procedure 150, various and multiple registrations can occur via fiducial or fiducial marker-less systems, including those discussed above. The method 150 is described in relation to a selected procedure, such as a cranial or deep brain stimulation procedure, but can be used for any appropriate procedure on the anatomy. Therefore, the discussion herein relating to a cranial or deep brain stimulation procedure is merely exemplary.

Briefly, the method 150 can be used to perform a first registration of the image space to the physical space, perform a first procedure, perform a second registration, and perform a second procedure. The two separate registrations can be used to account for the differing accuracies that can be used in performing the two separate procedures. For example, a first procedure can be performed with a first registration accuracy and a second procedure can be performed with a second greater registration accuracy.

The method 150 starts at start block 152. At block 154 image data acquisition of the patient is performed block 154. The image data acquired of the patient can be any appropriate image data such as image data acquired with the imaging device 34. Although, any appropriate imaging device can be used such as a magnetic resonance imaging device, a computed tomography imaging device, an ultrasound imaging device, or any appropriate imaging device. The acquired image data can be acquired preceding a procedure or during a procedure. In addition, the image data acquired in block 154 can be acquired at any appropriate time. Further, the patient 14 can have fiducial points associated with the patient, such as the fiducial markers 58 or any other appropriate fiducial markers. Moreover, the image data acquired in block 154 can be registered to the patient space according to various techniques, including those discussed above, without the use of fiducial markers.

As discussed above, the patient 14 can have fiducial markers, such as the fiducial markers 58 associated therewith. The fiducial makers 90 can be any appropriate fiducial marker such as fiducial markers that can act both as image-able fiducial markers to create fiducial points in image data and fiducial markers that can be touched or found in physical space. For example, fiducial markers can include the markers sold by IZI Medical Products of Baltimore, Md. The fiducial markers can include a portion that can be imaged with a selected imaging process and can also be found in physical space. Finding the image data portion defining the fiducial marker and correlating it to the fiducial marker in physical space can allow for registration.

It will also be understood that including a fiducial marker with the patient 14 during imaging may not be required. For example, the Tracer® registration system, Fazer® Contour Laser, the skin penetrating laser 102, the sheets 120, 140, or the like can be associated or used to determine the contour of the patient 14 after the image data is acquired. As discussed above, various contour matching algorithms can be used to match or register the physical space of the patient 14 to the image data. Therefore, although fiducial markers can be associated with the patient 14, fiducial markers are not required for registration of a physical space to the image space and a fiducial marker-less registration can also be performed.

After the image data is acquired, or concurrently or prior thereto, the patient can be positioned for the procedure in block 156. A first dynamic reference frame including a tracking device 34*d* can be associated with the patient 14 in a substantially non-permanent or non-invasive manner. The dynamic reference frame including a tracking device 34*d* can be associated with and attached to the patient with a first holder 160. The first holder 160 can be an easily removable and non-invasive, such as the Fess Frame™ holding device sold by Medtronic, Inc. Generally the first holder 160 can be efficiently removed, at least in part due to the surface contact members or holding members 162, such as suction cups or anti-slip feet. The surface contact member 162 generally contacts a surface of the patient 14, such as an outer surface of the skin of the patient 14. The first holder 160 can be associated with the patient 14 in any appropriate manner, such as after positioning the patient 14 for a procedure and positioning the first holder 160 on the patient's cranium 60.

The course registration can include a selected accuracy, such as about +/−0.5 to about +/−3 millimeters, including about +/−1 to about +/−2 millimeters in navigational accuracy. The accuracy achieved of the registration with the first holding device 160 can be appropriate for identifying a planned position for a burrhole 164. As discussed herein, the planned position of the burr hole 164 can be identified relative to the patient 14 within a selected accuracy that can be less than the required accuracy for navigating a lead or device into the patient 14.

After the dynamic reference frame is associated with the patient in block 158, position information can be acquired of the patient in block 170. The position information acquired of the patient in block 170 can include the identification of locations of fiducial markers, such as the fiducial markers 58 on the patient 14. As discussed above, the identification of the location of the fiducial markers 58 on the patient 14 can be performed by tracking the device 12 and touching or associating it with one or more of the fiducial markers 58. The navigation system 10 can then register the patient space to the image space, as discussed above.

In addition, various fiducial marker-less registration techniques can be used, including those discussed above. For example, the Tracer® registration system and Fazer® Contour Laser can be used to identify contours of the patient 14 to allow for a contour matching and registration to the image space. In addition, the skin penetrating laser system 100 can be used to identify various virtual fiducial points 108 on the patient 14 to assist in the identification of various points and identify contours of the patient 14, again for registration. Further, the various drapes or sheets 120, 140 can include a plurality of the tracking devices or coils to provide information relating to positions or contours of the patient 14. Therefore, the patient space can be registered to the image space according to any appropriate technique including identifying contours of the patient 14 for registration to image data acquired of the patient in block 154.

Once position information of the patient is acquired in block 170, a first or course registration can occur in block 172. As discussed above, the registration using the acquired position information in block 170 and the first dynamic reference frame associated with the patient in block 158 can include a selected registration accuracy. The registration accuracy can be any appropriate accuracy such as about 1 millimeter or greater. The accuracy achieved with the first dynamic reference frame attached in block 158 can be used for various portions of the procedure, such as identifying the planned entry portal or burrhole location 164 on the patient 14. As is understood by one skilled in the art, the planned location of the entry portal 164 can be identified on the image data acquired in block 154. Once the image space is registered to the physical space, the planned position of the entry portal 164 can be transferred to the patient 14. This allows the determination of an appropriate position for the entry portal into the patient in block 174. The planned position for the entry portal can be marked on the patient in block 176. Due to the registration accuracy with the first dynamic reference frame position of the entry portal will include a similar accuracy.

The entry portal can include a selected accuracy or lack of accuracy for various reasons. For example, a navigation frame, such as the Nexframe® stereotactic system sold by Medtronic, Inc. can include a selected amount of navigational positioning or movement. Therefore, according to various embodiments, if the marking of the entry portal on the patient 14 is within a selected accuracy, the guiding device can be positioned to achieve an appropriate trajectory of an instrument into the patient 14. It will be understood that the guiding device need not be used in navigating an instrument.

After the planned position of the entry portal, as marked in block 176, the first dynamic reference frame may be optionally removed in block 178. It will be understood that the first dynamic reference frame can remain on the patient 14 during a complete procedure and removal of the first DRF is merely optional. Removal of the first DRF, however, can allow for easy or efficient access to various portions of the patient 14 by the user 60.

The entry portal can then be formed in the patient 14 in block 180. The entry portal 182 can be formed near or at the planned position 164. The entry portal 182 can be formed using any appropriate instruments, such as a generally known burrhole forming device to form at the entry portal 182 into the patient 14. After the entry portal is formed in the patient a guiding or alignment device 185 including a base 186 can be associated with the patient near the entry portal in block 184. The guiding device 185 can be any appropriate guiding device, including the NexFrame™ frame sold by Medtronic, Inc. Nevertheless, any appropriate guiding device can be used, such as a stereotactic head frame, including the Leksell® Stereotactic System head frame sold by the Elekta AB of Sweden. An instrument 187 can be guided with the guiding device 185. Alternatively, a guiding device need not be used and an instrument or appropriate device can be independently navigated into the patient 14 without a guide device.

A second dynamic reference frame 190 can be associated with the patient 14 or the guiding device 185 in block 188. The second dynamic reference frame 190 can be formed with the guiding device 186, affixed to the guiding device 186, or positioned in an appropriate manner. The second dynamic reference frame 190 can be integrally formed with the guiding device 186 or interconnected with the guiding device 186. For example, an EM tracking device can be associated or formed with a starburst connector to be connected to the guiding device. Starburst type connectors can include those disclosed in U.S. patent application Ser. No. 10/271,353, filed Oct. 15, 2002, now U.S. Pat. App. Pub. No. 2003/0114752, incorporated herein by reference.

The second dynamic reference frame 190 can be substantially rigidly affixed to the patient 14 either directly or via the guiding device 186. As is understood, if the dynamic reference frame 190 is associated with the guiding device 186, the number of invasive passages or incisions into the patient 14 can be minimized. It will also be understood, that the second DRF 190 can be attached directly to the cranium 60 of the patient 14 rather than too the guide device 186. A bone engaging member can be used to mount the tracking device 34d directly to the bone of the cranium. Regardless, the second DRF 190 is generally invasively fixed to the patient 14.

Once the second dynamic reference frame 190 is fixedly associated with the patient 14, a second or fine registration can occur in block 192. The second registration performed in block 192 can use the same or different registration fiducial markers or a fiducial marker-less system, similar to the acquisition of position information in block 170. Then the registration of patient space to the image space in block 192 can include the acquisition of position information of the patient and registering to the image space.

The rigid association of the second DRF 190 with the patient 14, however, can maximize the accuracy of the registration. According to various embodiments, the accuracy of the second registration can be higher than the accuracy of the first registration by any appropriate amount. For example, the fine registration can be 1 time to 100 times more accurate, including 1 time to about 10 times more accurate. For example, the accuracy of the registration via the second DRF 190 can be less than about +/−1 millimeter. For example, the accuracy can be about +/−0.1 millimeters to about +/−0.9 millimeters. The accuracy of the fine registration can allow for substantially precise navigation or positioning of instruments or devices relative to the patient 14. For example, navigation of the guide device 186 can be substantially precise to allow the navigation of a selected instrument or therapeutic device 194. The accuracy of the registration allows for the accuracy of the navigation and positioning of various portions relative to the patient 14.

Once the second registration occurs using or having the appropriate accuracy, the procedure can be navigated in block 196. The navigation of the procedure in block 196 can be any appropriate navigation such as navigation of a deep brain stimulation electrode, a micro-electrode electrode for recording, an implant, a navigation of a therapy delivering device (e.g. catheter), or any appropriate instrument or procedure. The procedure that can then be completed in block 198, such as implanting a deep brain stimulation electrode and fixing it with a Stimloc® lead anchoring device sold by Medtronic, Inc. or Image-Guided Neurologics, of Florida.

Once the procedure is completed in block 198, a decision block whether a bilateral procedure is to be performed can occur in block 200. If YES is determined in block 202 the formation of an entry portal in block 180 can be performed again at a second location, such as at a bilateral location of the patient 14. If a bilateral procedure is not occurring, the result block NO 204 can be followed and the procedure can be ended in block 206. Ending the procedure can include various appropriate functions such as completing an implantation, closing the incision of the patient 14, or other appropriate steps. For example, after the implantation of the deep brain stimulation electrode, the stimulating device can be programmed according to any appropriate technique.

Figure 8:
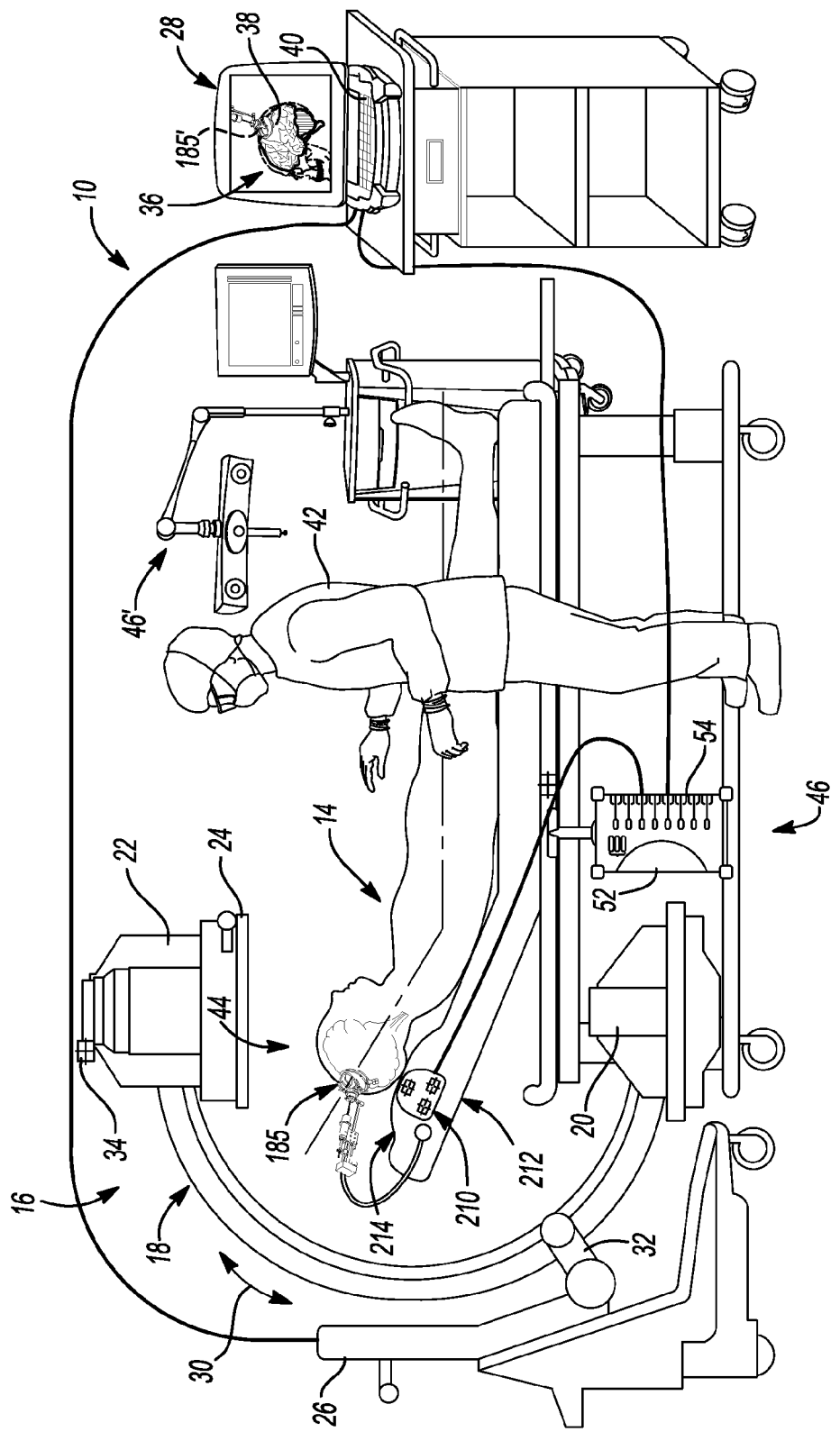
FIG. 8 is an environmental view of a navigation system, according to various embodiments.

With reference to FIG. 8, the procedure discussed above can be performed on the patient 14 using appropriate navigable instruments and devices. It will also be understood that the appropriate procedure can include electrical recording, deep brain stimulation probe placement, etc. A localizer 210 can be integrated or positioned into a portion of a patient support 212, such as a headrest, a bed, or the like. The localizer 210 can be positioned into the patient support 212 at any appropriate location. For example, the localizer 210 can be positioned in a headrest portion 214 of the patient support 212. The localizer 210 can then be used to generate a field relative to the patient, such as encompassing all or part of the patient's head. This placement can assist in providing or forming a navigation field in the patient space defined by the patient 14. For example, placing the localizer 210 into the headrest can form a field encompassing the cranium or skull 60 of the patient 14 with a small volume localizer, low power system, etc. Also, the localizer 210 can be integrated into the patient support 212 to reduce additional portions or pieces placed in operating room devices that need to be manipulated by the user 42. Therefore, the localizer 210 can be provided and the patient 14 can be positioned upon the patient support 212 at any appropriate time. Exemplary positioning elements that include localizer coils are also disclosed in U.S. patent application Ser. No. 10/405,068, filed Apr. 1, 2003, now published as U.S. Pat. App. Pub. No. 2004/0199072, published on Oct. 7, 2004, entitled "INTEGRATED ELECTROMAGNETIC NAVIGATION AND PATIENT POSITIONING DEVICE," incorporated herein by reference.

The localizer array 210 positioned within the patient support 212 can then be operated during a selected portion of a procedure. For example, the tracking system 46 can be used to operate the localizer array 210 to define a navigation field relative to the skull 60 of the patient 14 for various purposes, including those discussed herein. Integrating the localizer array 210 in the headrest removes a requirement of placing the localizer 210 near the skull 60 during the operative procedure, thereby eliminating a step of positioning a localizer. In addition, integrating the localizer array 210 into the headrest 214 can assist in minimizing movement of the localizer array 210 during a procedure.

The localizer array 210 can operate substantially similarly to the localizer array 48, 50 discussed above. An electromagnetic field can be generated to define a navigation area for navigating instruments and devices relative to the patient 14. Briefly, the localizer 210 can include one or more coils. Each of the coils can generate a navigation field, such as an electromagnetic field. In addition, each of the coils can include one or more coils, such as three mutually orthogonal coils. Thus, the localizer 210 can include nine total coils. Also, the localizer 210 can act as a receiver for fields generated by other coils. Thus, the localizer 210 can act as a generator or a receiver in the tracking system 42.

Figure 9:
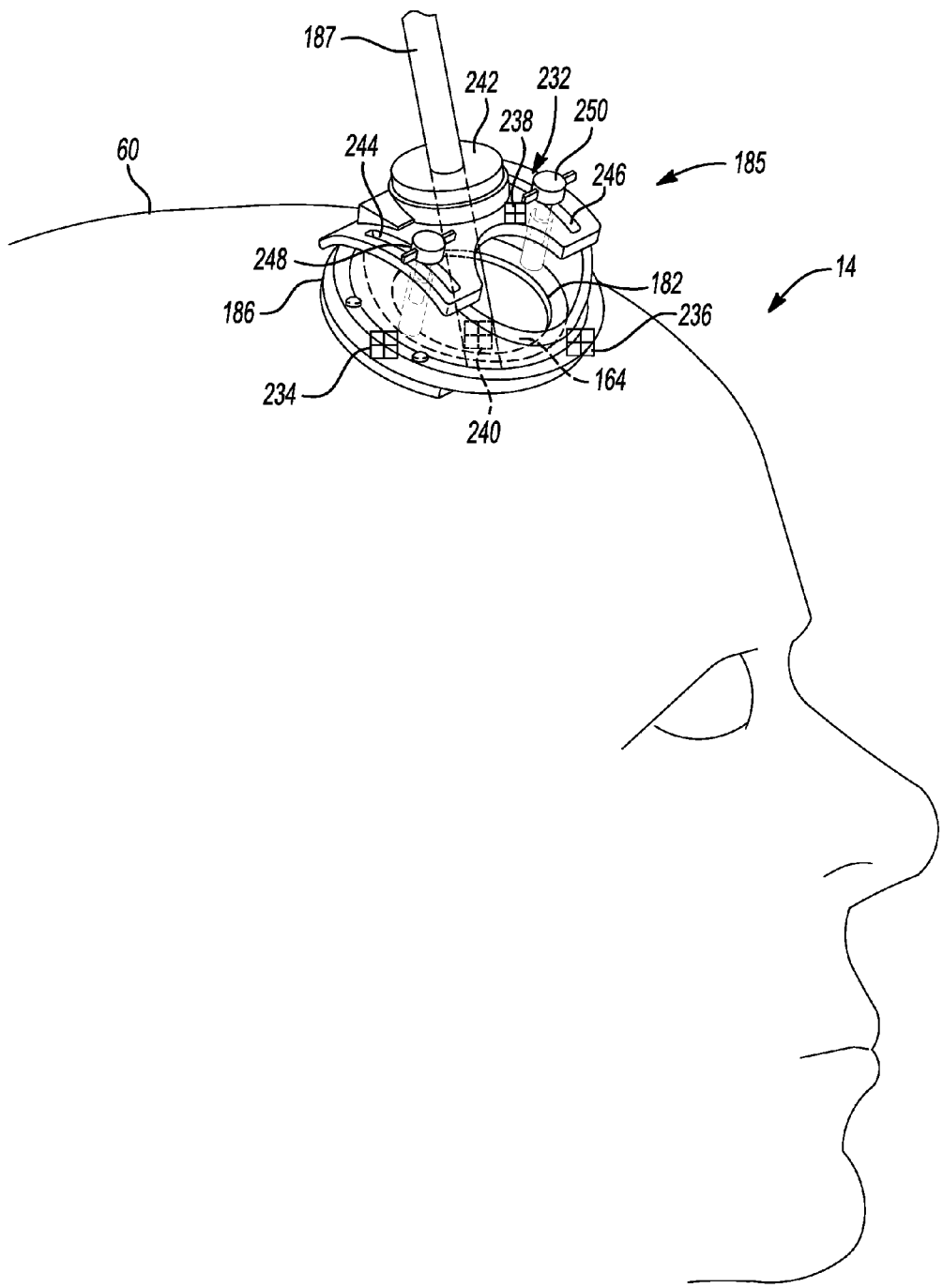
FIG. 9 is a detail environmental view of an alignment device including an EM coil, according to various embodiments.

With additional reference to FIG. 9, the alignment system 185 can be positioned on the skull 60 of the patient 14. The alignment system 185 can include various portions, but generally includes the base 186 and a trajectory guide portion 232. The alignment device 185 can be substantially similar to that discussed above and be positioned relative to the burr hole 164.

In addition, the alignment device 185 can include various electromagnetic coils (herein, EM coils) for use with the tracking system 46. The alignment device 185 can include a first EM coil 234 that is fixed or positioned within the base 186. The base 186 can also optionally include a second EM coil 236. The trajectory portion 232 can further include a third EM coil 238. The EM coils 234, 236, 238 can be used for various purposes, as discussed further herein, including tracking the position of the base 186 and the trajectory guide 232. The EM coils can also be used as field generating coils for various reasons, such as guiding the instrument 187. Accordingly, the EM coils 234, 236, 238 can both generate a field and receive or sense a field generated by other coils, similar to the coils of the localizer 210. It will also be understood, that the coils of the system can be used in reverse of specifically described here. In other words, the first EM coil 234 can either sense a field generated by another localizer coil 210 or the first EM coil 234 can transmit a field to be sensed by the localizer coil 210. In either case, the position of the first EM coil 234 in the base 186 can be determined and this determination can be used for navigation of the base 186. Similar methods can be applied to navigating any other coils according to various embodiments.

In addition, reference to the coils 234, 236, 238 will be understood to include a single coil or more than one coil positioned relative to a second coil, such as orthogonally to one another. For example, each of the EM coils 234, 236, 238 can include three coils positioned orthogonally to one another.

The instrument 187 can also include a tracking sensor EM coil 240. The coil 240 on the instrument can be formed as one or more coils, as well. The instrument 187 can include one or more members. For example, the instrument can include a guide tube in which another device, such as a deep brain stimulation probe or micro-electrode recorder, can be positioned. Thus, the instrument 187 can include a first portion that can be fixed in the trajectory portion 232 while another instrument portion moves within the tube. IN the alternative, the instrument 187 can be a single member. In the latter case, one or more EM coils can be positioned on both the tube and the instrument moveable within the tube. The multiple coils, on the instrument, base 186, or of the localizer 210 can allow for at least six-degree-of-freedom location determination.

The user 42 can position the alignment system 185 onto the patient 14 for a selected procedure. During positioning of the alignment device 185 onto the patient 14, the localizer array 210, within the patient support 212, can form a navigation field to assist in navigating the alignment device 185 onto the patient 14. Positioning the alignment device 185 onto the patient 14 can then be performed substantially precisely. The burr hole 164 can be formed before or after positioning the alignment device 185 on the patient 14 and navigating or guiding the alignment device 185 relative to the patient 14 can assist in ensuring an appropriate location of the alignment device 185 relative to the patient 14.

The alignment device 185 can be positioned on the patient 14 according to a plan or at predetermined location. As discussed above, the image data can be acquired of the patient 14 including the skull 60. The image data or any appropriate portion can be used to plan or predetermine the location for the alignment device 185. The navigation system 10 can, however, be used to navigate and track the position of the alignment device 185 relative to the patient 14, as discussed further herein. The position of the alignment device 185 can be displayed on the display 36 relative to the image data 38, which can include an image of the skull 60.

The alignment device 185 can include any appropriate alignment device, such as the Nexframe® alignment device. Other appropriate alignment devices 185, however, can be positioned relative to the patient 14 to achieve a selected position of the trajectory guide 232 relative to the patient 14.

The trajectory guide 232, however, can be positioned precisely relative to the patient 14 in a more efficient manner when the alignment device 185 is positioned at a selected location relative to the patient 14. For example, the trajectory guide 232 may be allowed to moved only through a range of motion, such as 30-60 degrees. Therefore, the 30-60 degrees of motion provides limits to the amount of trajectory of the instrument 187 can achieve relative to the patient 14 from any one location of the alignment device. Therefore, the trajectory guide 232, having the selected range of movement, can be positioned relative to the patient 14 to ensure an appropriate trajectory can be formed with the instrument 187.

Therefore, the localizer array 210 can be used to position the alignment device 185 relative to the patient 14. As discussed above, the localizer 210 can include one or more coils that can generate or sense a field. Thus, the various EM coils 234, 236, 238 on the alignment device 185 can act as tracking sensors, in concert with the localizer 210 during the positioning of the alignment device 185 relative to the patient 14.

Figure 10:
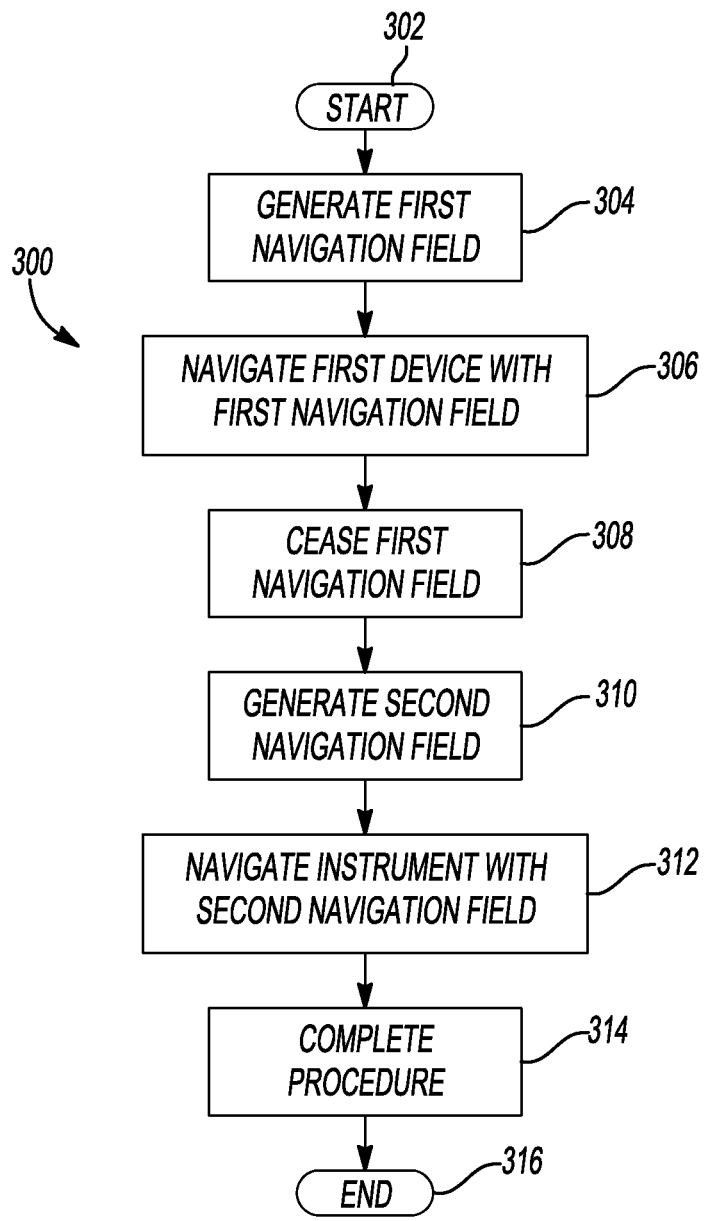
FIG. 10 is a flow chart of a method of performing a procedure, according to various embodiments.

The localizer 210 can create a first navigation or tracking field, as discussed further herein and illustrated in FIG. 10. The position of the EM coils 234, 236, 238 can be determined with the tracking system 46 using the first navigation field. The determined position of the alignment device 185 can be illustrated on the display 28 as icon or graphical representation 185'. Thus, the EM coils 234, 236, 238 can be tracked or the location of the coils can be determined with the tracking system 46 for determining the location of the alignment device 185.

The alignment device 185 can be fixed to the patient 14 in any appropriate manner. For example, one or more bone screws can be used to fix the alignment device 185 to the patient. Once fixed to the patient at least a portion of the alignment device 185 is substantially immovable relative to the patient 14. For example, the base 186 is substantially fixed relative to the patient 14 while the trajectory guide portion 232 may be able to move relative to the patient 14, at least during a selected portion of the procedure. Therefore, at least the EM coil 234 and the optional EM coil 236 are substantially fixed relative to the patient 14 once the base 186 of the alignment device 185 is fixed to the patient 14. The EM coils 234, 236, once the base 186 is fixed to the patient 14, can substantially define a dynamic reference frame or fixed EM coil relative to the patient 14.

If two coils are provided on the base 186, such as the first coil 234, and the second coil 236, the known position of the first coil 234 relative to the second coil 236 can be used to determine integrity of the field formed for navigation, such as the field defined by the localizer array 210. The integrity can include ensuring that a known position of the coils is being determined. If the determined position is different than a known or previous position it may indicate that there is an error or distortion in the generated field, such as interference from another metal object. It can also indicate that the instrument or device has been altered or damaged. Thus, integrity of the instruments or devices used in a procedure and the fields generated in the procedure an be checked or confirmed.

As discussed above, in an EM tracking system, the field provided by the localizer array 210 can include an electromagnetic field, which is measured or sensed by the EM coils 234, 236. Therefore, if a known relative location of the EM coils 234, 236 is known, the measured distance of the first EM coil 234 relative to the second coil 236 can be used by the workstation 28 to ensure an integrity of the field formed by the localizer array. It will be further understood, that a known position of the EM coil 238 on the trajectory guide 232 can also be used relative to either of the EM coils 234, 236 to determine integrity of the EM field.

In addition, the EM coils 234, 236, which are substantially fixed to the patient 14 due to their integration into the base 186, can also form a field relative to the instrument 187 and the trajectory guide EM coil 238. The field generated by the coils 234, 236, 238 of the alignment device can generate a second navigation field, as discussed further herein and illustrated in FIG. 10. Therefore, the coils 234, 236 formed in the base 186 can also act as localizer coils, at least during a portion of a procedure relative to the patient 14. Because the EM coils 234, 236 are fixed relative to the patient 14, fields produced by the coils are also fixed relative to the patient 14. It will be understood, that the EM coils 234, 236 can be powered through any appropriate mechanism, such as a cable, a power signal, a power cell, or the like to produce a field that can be sensed with the coils 238, 240 on the trajectory guide 232 or the instrument 187, respectively.

During an operative procedure, the EM coil 240 on the instrument 187 can be used as a tracking sensor to determine the location of any portion of the instrument 187. In addition, the EM coil 238 on the trajectory guide 232 can be used to determine the trajectory or the position of the trajectory guide 232. It will be understood that the tracking sensors 240, 238 can be positioned at any appropriate location. For example, the tracking sensor 238 can be positioned substantially near or on an adapter 242 positioned in the trajectory guide 232.

The trajectory guide 232 can move relative to the base 186 via a track or slot 244, 246 defined by the trajectory guide 232. Thus, the trajectory guide 232 can be guided or navigated to a selected location or orientation relative to the burr hole 164 defined in the patient 14. The trajectory guide 232 can then be fixed in place via any appropriate mechanism, such as one or more locking screws 248, 250.

Once a trajectory is selected, the instrument 187 can be moved relative to the trajectory guide 232. Movement of the instrument 187 relative to the trajectory guide can be performed in any appropriate manner, such as via the user 42, the drive system, a robot, or any other appropriate mechanism. Appropriate drive mechanisms include the Nexdrive® driving and positioning device sold by Medtronic, Inc. having a place of business in Colorado, USA. Regardless, the tracking sensor 240 of the instrument 187 can be tracked with a navigation field that can be created by various EM coils, such as the coils of the localizer 210 or the coils 234, 236 provided in the base 186.

The coils 234, 236 of the base 186 can be formed in the base as substantially a single piece. For example, the base 186 can be molded of plastic or polymer and the coils 234, 236 can be molded into the base 186. In addition, or alternatively, the coils 234, 236 can be welded, fixedly adhered, or any other appropriate mechanism can be used for fixing the coils 234, 236 to the base 186. The coils 234, 236, however, can be substantially fixedly positioned relative to the base 186. Regardless, the coils 234, 236 can be positioned on or in the base substantially directly so that a separate connection mechanism is not necessary or provided. Fixedly providing the coils 234, 236, either molded into or formed with the base, 186 can eliminate inadvertent movement of the coils 234, 236, inappropriate adjustments of the coils 234, 236, or operative time in positioning the coils 234, 236 on the base 186. It can also assist in properly navigating or guiding the base 186 relative to the patient 14 and also allow for use of the coils 234, 236 as localizing emitters.

In addition, the third EM coil 238 can be substantially integrated into the trajectory guide 232. The trajectory guide 232 can also be formed as a polymer or plastic material and the coil 238 can be molded with the trajectory guide 232 during formation of the trajectory guide 232. The integration or co-forming of the coil 238 and the trajectory guide 232 can also reduce inadvertent movement, incorrect attachments, and other issues with providing a separate or distinct EM coil from the trajectory guide 232.

The additional coil 240 can also be integrated or formed with the instrument 187 as one piece or member. The coil 240 can be used to determine a position and orientation or only a depth of the instrument 187. For example, once the trajectory portion 232 is fixed in a position the instrument 187 may only be able to move axially. Thus, its trajectory is known and its position along the axis can be determined and illustrated on the display 28.

Therefore, the EM coils 234, 236, 238 can be formed with the alignment device 185 to allow for a substantially rigid and fixed position of the EM coils 234, 236, 238 of the alignment device 185. In addition, the alignment device 185, therefore, can be navigated with a different localizer, such as the localizer 210, and then further define the navigation field for navigating the instrument 187 relative to the patient 14. The coils of the base 186 can be used to provide a navigation field at least, in part, because the position of the base 186 is known relative to the patient 14 due to navigating the base 186 relative to the patient 14 with the localizer 210. Therefore, the tracking system 46 is used to determine the position of the base 186 of the alignment device 185 to allow the EM coils 234, 236 to be used as localizer coils for a portion of the procedure, such as navigating the instrument 187 relative to the patient 14. It will be understood, however, that the localizer 210 can also be used in combination with the coils 234, 236 of the base for positioning or tracking other coils, such as the coils 238, 240 in the trajectory guide 238 and the instrument 187, respectively.

One skilled in the art will understand that the processes and systems discussed above can be used in a surgical procedure. The processes and systems, however, are understood to not be limited to use during or with a surgical procedure. The systems and processes can be used to acquire information regarding inanimate objects, inform or build a database of information; plan a procedure; formulate teaching aids, etc. Registration of image space to physical space can be performed relative to any object in physical space, including a patient, an inanimate object, etc. Also, the registration can occur for any appropriate reason, which may or may not be a surgical procedure.

With reference to FIG. 10, and FIGS. 8-9, the alignment device 185 can be positioned relative to the patient 14 and the instrument 187 can be guided relative to the patient 14, according to a method 300. The method 300 can start in start block 302. A first navigation field or localizer field can then be generated in block 304. A first device, such as the alignment device 185, can be navigated relative to the patient 14 using the first navigation field in block 306. As discussed above, for example, in relation to FIG. 8, the first navigation field can be formed with the localizer system 210. The localizer system 210 can be positioned substantially near the skull 60 of the patient 14 for producing a field generally in the area of navigating the alignment device 185 relative to the patient 14.

Once the first device has been navigated with the first navigation field, the first navigation field can be ceased in block 308. For example, once the alignment device 185 is mounted relative to the patient 14, the first navigation field can be ceased. If further portions or procedures are required, however, a second navigation field can be generated in block 310. As discussed above, the generation of the second navigation field can be formed with the EM coils 234, 236 associated with the base 186 of the alignment device 185. Therefore, the second navigation field can be generated with coils that are separate from the coils that generate the first navigation field in block 304.

The generation of the second navigation field can also include lower power or volume for various purposes. For example, the second navigation field can be generated to substantially include only a volume or area in which the instrument 187 can or is planned to be guided with the alignment device 185. It will also be understood that the coils may work in reverse to the above. For example, a first coil can sense a second field encompassing at least the head of the patient where a second coil generates the second field. The first coil can be positioned in or on the patient support, such as in the headrest, and the second coil can be associated with the alignment device 185, such as with integrated into the base of the alignment device 185. Accordingly, the navigation system 10 can be used to determine the location of a tracking device or coil if it is either generating a field that is sensed or sensing a field generated by another coil.

Therefore, the instrument 187 can be navigated with the second navigation field in block 312. The instrument 187 can be navigated in block 312 for any appropriate procedure, such as movement of an instrument into the skull 60 of the patient 14. Exemplary procedures include placement of the DBS, fixation of the lead, micro-recording, or the like.

The procedure can then be completed in block 314. The completion of the procedure in block 314 can include any appropriate steps or procedures, such as closing an incision, mounting a lead, or the like. The procedure method can then end in block 316. Therefore, it will be understood, that the procedure can allow for navigation of two or more instruments with two or more navigation fields. Moreover, the second navigation field can be generated after ceasing the first navigation field. Therefore, two different devices, such as the alignment device 185 and the instrument 187, can be navigated relative to the single patient 14 using two different navigation fields generated at two different times and by two different coils.

In addition, the two fields can be generated for various purposes. For example, the first navigation field can be generated to encompass substantially only the skull 60 of the patient 14. This can help reduce possible interference, reduce power, etc. for generating the field. The second navigation field can then be generated substantially only to encompass an area for navigation of the instrument 187. This, again, can help reduce interference in the field, etc. Thus, both of the navigation fields can be generated for various purposes and to achieve selected results, such as reduced interference, high field integrity, and navigational accuracy.

Also, the coils as a part of the alignment device 185 can provide further efficiencies. It can assist in the flow of the procedure by reducing system components and steps for performing a procedure. This can also streamline the piece-parts of the navigation system 10. The navigation system 10 including coils on the alignment device 185 can be used to reduce components and workflow for a procedure using the navigation system 10, as discussed above.

The teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A surgical navigation system, comprising:
   a head support portion configured to support at least a head of a patient;
   a processor operably associated with a first coil, a second coil and a third coil;
   the first coil positioned within the head support portion and configured to generate a first navigation field encompassing a volume relative to the patient;
   an alignment device including a base configured to be connected directly to the head of the patient;
   the second coil integrated into the base of the alignment device, wherein the second coil is configured to sense the first navigation field produced by the first coil; and
   the third coil being coupled to an instrument;
   wherein the processor is configured to cooperate with at least the second coil and the third coil to determine a position of the instrument, and wherein the processor is configured to drive the first coil to generate the first navigation field and the second coil to generate the second navigation field independently such that the second navigation field is generated after ceasing the first navigation field.

2. The surgical navigation system of claim 1, further comprising a patient support that includes a bed portion configured to support at least a portion of a torso of the patient and the head support portion.

3. The surgical navigation system of claim 1, wherein the first coil includes at least three electromagnetic coils configured to form the first navigation field.

4. The surgical navigation system of claim 3, wherein the second coil integrated into the base is configured to generate a second navigation field to encompass at least a portion of the head of the patient; and
   wherein the third coil is configured to sense the second navigation field.

5. The surgical navigation system of claim 4, wherein the third coil is configured to sense the first navigation field, the second navigation field, or combinations thereof; and
   wherein the processor is configured to cooperate with the third coil to determine the location of a first instrument portion independently moveable relative to the base, a location of a second instrument portion moveable relative to a third instrument portion, or combinations thereof.

6. The surgical navigation system of claim 1, further comprising an imaging device configured to obtain image data of the patient.

7. The surgical navigation system of claim 6, further comprising a display device configured to display the image data of the patient, the display device further configured to display a graphical representation of at least the alignment device, the instrument, or combinations thereof relative to the image data.

8. The surgical navigation system of claim 7, wherein the processor is configured to process data to determine a tracked location of the alignment device, the instrument, or combinations thereof for display on the display device.

9. The surgical navigation system of claim 1, further comprising a fourth coil integrated into the base, wherein the processor is configured to independently determine a position of the second coil and the fourth coil to at least check an integrity of the first navigation field, the base, the alignment device, the instrument, or combinations thereof.

10. A surgical navigation system, comprising:
    a processor operably associated with a first coil, a second coil, a third coil, and a fourth coil;
    the first coil configured to generate a first navigation field encompassing a volume relative to a patient;
    an alignment device including a base member and a trajectory guide member, the base member configured to be connected directly to a head of the patient, the trajectory guide member selectively moveable relative to the base member and configured to guide an instrument relative thereto;
    the second coil coupled to the base member and configured to sense the first navigation field generated by the first coil;
    the third coil coupled to the trajectory guide member and configured to sense a second navigation field generated by the second coil such that the processor can determine a trajectory of the trajectory guide member relative to the base member, the second navigation field being generated independently of the first navigation field; and
    the fourth coil being coupled to the instrument;
    wherein the processor is configured to cooperate with at least the second coil and the fourth coil to determine a position of the instrument, and wherein the processor is configured to drive the first coil to generate the first navigation field and the second coil to generate the second navigation field substantially independently such that the second navigation field is generated after ceasing the first navigation field.

11. The surgical navigation system of claim 10, further comprising a head support portion configured to support at least the head of the patient, the first coil being fixed to the head support.

12. The surgical navigation system of claim 11, further comprising a patient support that includes a bed portion configured to support at least a portion of a torso of the patient, the head support portion integrated with the patient support.

13. The surgical navigation system of claim 10, wherein the first coil includes at least three electromagnetic coils configured to form the first navigation field.

14. The surgical navigation system of claim 10, wherein the fourth coil is configured to sense the first navigation field, the second navigation field, or combinations thereof; and
    wherein the processor is configured to cooperate with the fourth coil to determine a location of a first instrument portion independently moveable relative to the base member, a location of a second instrument portion moveable relative to a third instrument portion, or combinations thereof.

15. The surgical navigation system of claim 10, further comprising a fifth coil integrated into the base member, wherein the processor is configured to independently determine a position of the second coil and the fifth coil to at least check an integrity of the first navigation field, the alignment device, the instrument, or combinations thereof.

16. The surgical navigation system of claim 10, wherein the processor is configured to drive the first coil to generate the first navigation field to encompass only a head of the patient, and to drive the second coil to generate the second navigation field so as to encompass only a range of motion of the instrument.

17. The surgical navigation system of claim 10, further comprising:
- an imaging device configured to obtain image data of the patient; and
- a display device configured to display the image data of the patient, the display device further configured to display a graphical representation of at least the alignment device, the instrument, or combinations thereof relative to the image data.

18. A surgical navigation system, comprising:
- a processor operably associated with a first coil, a second coil, a third coil and a fourth coil;
- the first coil associated with a head support portion of a patient support, the processor configured to drive the first coil to generate a first navigation field;
- an alignment device including a base member and a trajectory guide member, the base member configured to be connected directly to a head of the patient, the trajectory guide member selectively moveable relative to the base member and configured to guide an instrument relative thereto, the second coil integrated into the base member and configured to sense the first navigation field generated by the first coil;
- the third coil being fixed to the trajectory guide member and configured to sense a second navigation field generated by the second coil such that the processor can determine a trajectory of the trajectory guide member relative to the base member; and
- the fourth coil being coupled to the instrument;
- wherein the processor is configured to drive the second coil to generate the second navigation field independently of the first navigation field;
- wherein the processor is configured to cooperate with at least the second coil and the fourth coil to determine a position of the instrument, and wherein the processor is configured to control the second coil to sense the first navigation field at a first time to facilitate guiding the alignment device relative to the patient, and to drive the second coil to generate the second navigation field at a second time after the first coil ceases generating the first navigation field.

19. The surgical navigation system of claim 18, wherein the second coil is configured to cooperate with the third coil and the fourth coil such that the processor can determine a trajectory of the instrument guided by the trajectory guide member and an axial position of the instrument relative to the trajectory guide member or the base member.

20. The surgical navigation system of claim 18, wherein the processor is configured to drive the first coil to generate the first navigation field to encompass the head of the patient, and to drive the second coil to generate the second navigation field of the second size so as to encompass only a range of motion of the instrument.

21. The surgical navigation system of claim 18, further comprising:
- an imaging device configured to obtain image data of the patient; and
- a display device configured to display the image data of the patient, the display device further configured to display a graphical representation of at least the alignment device, the instrument, or combinations thereof relative to the image data.

22. The surgical navigation system of claim 1, wherein the patient support includes a bed portion configured to support at least a portion of a torso of the patient, the head support portion integrated with the patient support, the first coil being positioned within the head support portion.

* * * * *